United States Patent
Kroh et al.

(10) Patent No.: US 8,896,324 B2
(45) Date of Patent: *Nov. 25, 2014

(54) SYSTEM, APPARATUS, AND METHOD FOR IN-VIVO ASSESSMENT OF RELATIVE POSITION OF AN IMPLANT

(75) Inventors: Jason Kroh, Villa Rica, GA (US); Florent Cros, Decatur, GA (US); Christophe Courcimault, Avondale Estates, GA (US)

(73) Assignee: CardioMEMS, Inc., Atlanta, GA (US)

( * ) Notice: Subject to any disclaimer, the term of this patent is extended or adjusted under 35 U.S.C. 154(b) by 446 days.

This patent is subject to a terminal disclaimer.

(21) Appl. No.: 13/245,553

(22) Filed: Sep. 26, 2011

(65) Prior Publication Data

US 2012/0016228 A1    Jan. 19, 2012

Related U.S. Application Data

(60) Continuation of application No. 12/416,904, filed on Apr. 1, 2009, now Pat. No. 8,026,729, which is a continuation-in-part of application No. 11/613,645, filed on Dec. 20, 2006, now Pat. No. 7,550,978, which is a continuation of application No. 11/105,294, filed on Apr. 13, 2005, now Pat. No. 7,245,117, application No. 13/245,553, which is a continuation-in-part of application No. 11/717,967, filed on Mar. 14, 2007, now Pat. No. 7,466,120, which is a continuation-in-part of application No. 11/276,571, filed on Mar. 6, 2006, now Pat. No. 7,498,799, which is a continuation-in-part of application No. 11/105,294, filed on Apr. 13, 2005, now Pat. No. 7,245,117, said application No. 11/717,967 is a continuation-in-part of application No. 12/175,803, filed on Jul. 18, 2008, which is a division of application No. 11/472,905, filed on Jun. 22, 2006, now Pat. No. 7,574,792, which is a division of application No. 10/943,772, filed on Sep. 16, 2004, now abandoned, application No. 13/245,553, which is a continuation-in-part of application No. 11/157,375, filed on Jun. 21, 2005.

(60) Provisional application No. 60/623,959, filed on Nov. 1, 2004, provisional application No. 60/782,313, filed on Mar. 14, 2006, provisional application No. 60/503,745, filed on Sep. 16, 2003.

(51) Int. Cl.
*G01R 27/04* (2006.01)
*A61B 5/055* (2006.01)
*A61B 5/00* (2006.01)
*A61B 5/05* (2006.01)
*H01Q 7/00* (2006.01)
*A61B 5/07* (2006.01)

(52) U.S. Cl.
CPC ............... *A61B 5/055* (2013.01); *A61B 5/0031* (2013.01); *A61B 5/05* (2013.01); *H01Q 7/00* (2013.01); *A61B 5/076* (2013.01); *A61B 5/4514* (2013.01); *A61B 2560/0219* (2013.01); *A61B 2560/0223* (2013.01)
USPC ............ 324/633; 324/635; 324/655; 600/424

(58) Field of Classification Search
USPC ......... 324/633, 635, 652, 655, 668, 675, 682; 600/424
See application file for complete search history.

(56) References Cited

U.S. PATENT DOCUMENTS 2,512,641 A   6/1950 Halstead
2,796,863 A   6/1957 Wittern
(Continued)

FOREIGN PATENT DOCUMENTS

AU    701577 B2    2/1999
AU    2004274005 A1    3/2005
(Continued)

OTHER PUBLICATIONS

Supplemental European Search Report and the European Search Opinion for European Application No. 09755451.3 (National Phase of PCT/US2009/039220) (dated Apr. 11, 2013).

(Continued)

*Primary Examiner* — Vincent Q Nguyen
(74) *Attorney, Agent, or Firm* — Ballard Spahr LLP

(57) ABSTRACT

A method for providing an in-vivo assessment of relative movement of an implant that is positioned in a living being is provided wherein a first assembly and a second assembly are positioned within the living being. The first assembly includes a passive electrical resonant circuit that is configured to be selectively electromagnetically coupled to an ex-vivo source of RF energy and, in response to the electromagnetic coupling, generates an output signal characterized by a frequency that is dependent upon a distance between the first assembly and the second assembly at the time of the electromagnetic coupling.

26 Claims, 14 Drawing Sheets

(56) References Cited

U.S. PATENT DOCUMENTS

| | | |
|---|---|---|
| 3,419,384 A | 12/1968 | Rembaum |
| 3,419,834 A | 12/1968 | McKechnie |
| 3,550,137 A | 12/1970 | Kuecken |
| 3,651,243 A | 3/1972 | Hornor et al. |
| 3,867,950 A | 2/1975 | Fischell |
| 3,882,424 A | 5/1975 | Debois et al. |
| 3,913,028 A | 10/1975 | Bosselaers |
| 3,942,382 A | 3/1976 | Hok |
| 3,958,558 A | 5/1976 | Dunphy et al. |
| 4,026,276 A | 5/1977 | Chubbuck |
| 4,077,016 A | 2/1978 | Sanders et al. |
| 4,114,606 A | 9/1978 | Seylar |
| 4,127,110 A | 11/1978 | Bullara |
| 4,152,669 A | 5/1979 | Igarashi |
| 4,206,762 A | 6/1980 | Cosman |
| 4,207,604 A | 6/1980 | Bell |
| 4,207,903 A | 6/1980 | O'Neill |
| RE30,366 E | 8/1980 | Rasor et al. |
| 4,237,900 A | 12/1980 | Schulman et al. |
| 4,281,212 A | 7/1981 | Bogese, II |
| 4,354,506 A | 10/1982 | Sakaguchi et al. |
| 4,378,809 A | 4/1983 | Cosman |
| 4,385,636 A | 5/1983 | Cosman |
| 4,407,296 A | 10/1983 | Anderson |
| 4,424,403 A | 1/1984 | Bogese, II |
| 4,467,138 A | 8/1984 | Brorein |
| 4,485,813 A | 12/1984 | Anderson et al. |
| 4,494,950 A | 1/1985 | Fischell |
| 4,521,684 A | 6/1985 | Gilby et al. |
| 4,531,526 A | 7/1985 | Genest |
| 4,593,703 A | 6/1986 | Cosman |
| 4,596,563 A | 6/1986 | Pande |
| 4,617,606 A | 10/1986 | Shak et al. |
| 4,617,932 A | 10/1986 | Kornberg |
| 4,627,079 A | 12/1986 | von der Embse |
| 4,651,571 A | 3/1987 | McGlade |
| 4,660,568 A | 4/1987 | Cosman |
| 4,679,560 A | 7/1987 | Galbraith |
| 4,689,806 A | 8/1987 | von der Embse |
| 4,701,826 A | 10/1987 | Mikkor |
| 4,713,540 A | 12/1987 | Gilby et al. |
| 4,718,425 A | 1/1988 | Tanaka et al. |
| 4,720,687 A | 1/1988 | Ostoich et al. |
| 4,773,972 A | 9/1988 | Mikkor |
| 4,796,641 A | 1/1989 | Mills et al. |
| 4,815,472 A | 3/1989 | Wise et al. |
| 4,833,920 A | 5/1989 | Knecht et al. |
| 4,846,191 A | 7/1989 | Brockway et al. |
| 4,890,623 A | 1/1990 | Cook et al. |
| 4,899,752 A | 2/1990 | Cohen |
| 4,905,575 A | 3/1990 | Knecht et al. |
| 4,913,147 A | 4/1990 | Fahlstrom et al. |
| 4,924,172 A | 5/1990 | Holmgren |
| 4,934,369 A | 6/1990 | Maxwell |
| 4,987,897 A | 1/1991 | Funke |
| 5,036,854 A | 8/1991 | Schollmeyer et al. |
| 5,043,531 A | 8/1991 | Gutenson et al. |
| 5,113,868 A | 5/1992 | Wise et al. |
| 5,115,128 A | 5/1992 | Cook |
| 5,129,394 A | 7/1992 | Mehra |
| 5,148,123 A | 9/1992 | Ries |
| 5,153,583 A | 10/1992 | Murdoch |
| 5,165,289 A | 11/1992 | Tilmans |
| 5,173,836 A | 12/1992 | Tomase et al. |
| 5,181,423 A | 1/1993 | Philipps et al. |
| 5,192,314 A | 3/1993 | Daskalakis |
| 5,200,930 A | 4/1993 | Rouquette |
| 5,207,103 A | 5/1993 | Wise et al. |
| 5,265,606 A | 11/1993 | Kujawski |
| 5,277,068 A | 1/1994 | Fukiura et al. |
| 5,312,674 A | 5/1994 | Haertling et al. |
| 5,313,953 A | 5/1994 | Yomtov et al. |
| 5,331,453 A | 7/1994 | Lipsky |
| 5,353,800 A | 10/1994 | Pohndorf et al. |
| 5,355,714 A | 10/1994 | Suzuki et al. |
| 5,357,253 A | 10/1994 | Van Etten et al. |
| 5,373,852 A | 12/1994 | Harrison et al. |
| 5,400,535 A | 3/1995 | Schomaker |
| 5,411,535 A | 5/1995 | Fujii et al. |
| 5,411,551 A | 5/1995 | Winston et al. |
| 5,431,171 A | 7/1995 | Harrison et al. |
| 5,440,300 A | 8/1995 | Spillman, Jr. |
| 5,487,760 A | 1/1996 | Villafana |
| 5,491,299 A | 2/1996 | Naylor et al. |
| 5,497,099 A | 3/1996 | Walton |
| 5,515,041 A | 5/1996 | Spillman, Jr. |
| 5,535,752 A | 7/1996 | Halperin et al. |
| 5,538,005 A | 7/1996 | Harrison et al. |
| 5,551,427 A | 9/1996 | Altman |
| 5,554,139 A | 9/1996 | Okajima |
| 5,566,676 A | 10/1996 | Rosenfeldt et al. |
| 5,574,470 A | 11/1996 | de Vall |
| 5,593,430 A | 1/1997 | Renger |
| 5,594,389 A | 1/1997 | Kiyanagi et al. |
| 5,600,245 A | 2/1997 | Yamamoto et al. |
| 5,625,341 A | 4/1997 | Giles et al. |
| 5,626,630 A | 5/1997 | Markowitz et al. |
| 5,659,155 A | 8/1997 | Porzilli |
| 5,686,841 A | 11/1997 | Stolarczyk et al. |
| 5,695,155 A | 12/1997 | Macdonald et al. |
| 5,701,121 A | 12/1997 | Murdoch |
| 5,702,427 A | 12/1997 | Ecker et al. |
| 5,703,412 A | 12/1997 | Takemoto et al. |
| 5,703,576 A | 12/1997 | Spillman, Jr. et al. |
| 5,713,917 A | 2/1998 | Leonhardt et al. |
| 5,722,414 A | 3/1998 | Archibald et al. |
| 5,723,791 A | 3/1998 | Koch et al. |
| 5,740,594 A | 4/1998 | Lukasiewicz et al. |
| 5,743,267 A | 4/1998 | Nikolic et al. |
| 5,750,926 A | 5/1998 | Schulman et al. |
| 5,796,827 A | 8/1998 | Coppersmith et al. |
| 5,807,265 A | 9/1998 | Itoigawa et al. |
| 5,836,886 A | 11/1998 | Itoigawa et al. |
| 5,860,938 A | 1/1999 | Lafontaine et al. |
| 5,896,113 A | 4/1999 | O'Neill, Jr. |
| 5,899,927 A | 5/1999 | Ecker et al. |
| 5,905,575 A | 5/1999 | Matsuoka |
| 5,935,084 A | 8/1999 | Southworth |
| 5,942,991 A | 8/1999 | Gaudreau et al. |
| 5,967,986 A | 10/1999 | Cimochowski et al. |
| 5,974,894 A | 11/1999 | Delatorre |
| 5,976,070 A | 11/1999 | Ono et al. |
| 5,986,549 A | 11/1999 | Teodorescu |
| 6,009,350 A | 12/1999 | Renken |
| 6,015,386 A | 1/2000 | Kensey et al. |
| 6,015,387 A | 1/2000 | Schwartz et al. |
| 6,019,729 A | 2/2000 | Itoigawa et al. |
| 6,024,704 A | 2/2000 | Meador et al. |
| 6,025,725 A | 2/2000 | Gershenfeld et al. |
| 6,030,413 A | 2/2000 | Lazarus |
| 6,033,366 A | 3/2000 | Brockway et al. |
| 6,053,873 A | 4/2000 | Govari et al. |
| 6,076,016 A | 6/2000 | Feierbach |
| 6,111,520 A | 8/2000 | Allen et al. |
| 6,113,553 A | 9/2000 | Chubbuck |
| 6,134,461 A | 10/2000 | Say et al. |
| 6,140,740 A | 10/2000 | Porat et al. |
| 6,159,156 A | 12/2000 | Van Bockel |
| 6,165,135 A | 12/2000 | Neff |
| 6,198,965 B1 | 3/2001 | Penner et al. |
| 6,201,980 B1 | 3/2001 | Darrow et al. |
| 6,206,835 B1 | 3/2001 | Spillman, Jr. et al. |
| 6,208,305 B1 | 3/2001 | King |
| 6,212,056 B1 | 4/2001 | Gammel et al. |
| 6,237,398 B1 | 5/2001 | Porat et al. |
| 6,239,724 B1 | 5/2001 | Doron et al. |
| 6,252,163 B1 | 6/2001 | Fujimori et al. |
| 6,252,481 B1 | 6/2001 | Iwao et al. |
| 6,259,328 B1 | 7/2001 | Wesolowski |
| 6,277,078 B1 | 8/2001 | Porat et al. |
| 6,278,379 B1 | 8/2001 | Allen et al. |
| 6,287,253 B1 | 9/2001 | Ortega et al. |
| 6,291,343 B1 | 9/2001 | Tseng et al. |
| 6,292,104 B1 | 9/2001 | Wakabayashi |

(56) References Cited

U.S. PATENT DOCUMENTS

| | | |
|---|---|---|
| 6,298,271 B1 | 10/2001 | Weijand |
| 6,319,208 B1 | 11/2001 | Abita et al. |
| 6,327,319 B1 | 12/2001 | Hietala et al. |
| 6,331,792 B1 | 12/2001 | Tonietto |
| 6,338,284 B1 | 1/2002 | Najafi et al. |
| 6,373,264 B1 | 4/2002 | Matsumoto et al. |
| 6,383,144 B1 | 5/2002 | Mooney et al. |
| 6,409,674 B1 | 6/2002 | Brockway et al. |
| 6,411,130 B1 | 6/2002 | Gater |
| 6,416,474 B1 | 7/2002 | Penner et al. |
| 6,442,413 B1 | 8/2002 | Silver |
| 6,448,500 B1 | 9/2002 | Hosaka et al. |
| 6,454,720 B1 | 9/2002 | Clerc et al. |
| 6,495,895 B1 | 12/2002 | Peterson et al. |
| 6,517,483 B2 | 2/2003 | Park et al. |
| 6,533,733 B1 | 3/2003 | Ericson et al. |
| 6,548,176 B1 | 4/2003 | Gwo |
| 6,577,893 B1 | 6/2003 | Besson et al. |
| 6,625,341 B1 | 9/2003 | Novotny |
| 6,645,143 B2 | 11/2003 | VanTassel et al. |
| 6,656,135 B2 | 12/2003 | Zogbi et al. |
| 6,660,564 B2 | 12/2003 | Brady |
| 6,667,725 B1 | 12/2003 | Simons et al. |
| 6,678,458 B2 | 1/2004 | Ellis et al. |
| 6,682,490 B2 | 1/2004 | Roy et al. |
| 6,689,056 B1 | 2/2004 | Kilcoyne et al. |
| 6,702,983 B2 | 3/2004 | Hu et al. |
| 6,706,005 B2 | 3/2004 | Roy et al. |
| 6,743,173 B2 | 6/2004 | Penner et al. |
| 6,743,183 B1 | 6/2004 | Thornton |
| 6,749,574 B2 | 6/2004 | O'Keefe |
| 6,765,493 B2 | 7/2004 | Lonsdale et al. |
| 6,777,940 B2 | 8/2004 | Macune |
| 6,812,404 B1 | 11/2004 | Martinez |
| 6,822,570 B2 | 11/2004 | Dimmer et al. |
| 6,827,250 B2 | 12/2004 | Uhland et al. |
| 6,837,438 B1 | 1/2005 | Takasugi et al. |
| 6,855,115 B2 | 2/2005 | Fonseca et al. |
| 6,870,105 B2 | 3/2005 | Maydanich et al. |
| 6,890,300 B2 | 5/2005 | Lloyd et al. |
| 6,895,281 B1 | 5/2005 | Amundson et al. |
| 6,898,454 B2 | 5/2005 | Atalar et al. |
| 6,918,173 B2 | 7/2005 | Ahn |
| 6,919,240 B2 | 7/2005 | Uzawa et al. |
| 6,923,769 B2 | 8/2005 | Nishii et al. |
| 6,926,670 B2 | 8/2005 | Rich et al. |
| 6,929,974 B2 | 8/2005 | Ding et al. |
| 6,939,299 B1 | 9/2005 | Petersen et al. |
| 6,943,419 B2 | 9/2005 | Wong et al. |
| 6,943,688 B2 | 9/2005 | Chung et al. |
| 6,968,743 B2 | 11/2005 | Rich et al. |
| 6,989,493 B2 | 1/2006 | Hipwell, Jr. et al. |
| 7,005,056 B2 | 2/2006 | Srinivasan et al. |
| 7,024,936 B2 | 4/2006 | Pedersen et al. |
| 7,048,756 B2 | 5/2006 | Eggers et al. |
| 7,049,523 B2 | 5/2006 | Shuman et al. |
| 7,060,038 B2 | 6/2006 | Letort et al. |
| 7,076,215 B1 | 7/2006 | Moliere |
| 7,092,765 B2 | 8/2006 | Geske et al. |
| 7,147,604 B1 | 12/2006 | Allen et al. |
| 7,152,477 B2 | 12/2006 | Banholzer et al. |
| 7,181,261 B2 | 2/2007 | Silver et al. |
| 7,208,684 B2 | 4/2007 | Fetterolf, Sr. et al. |
| 7,215,991 B2 | 5/2007 | Besson et al. |
| 7,233,182 B1 | 6/2007 | Savoj |
| 7,245,117 B1 | 7/2007 | Joy et al. |
| 7,250,041 B2 | 7/2007 | Chiu et al. |
| 7,256,695 B2 | 8/2007 | Hamel et al. |
| 7,265,478 B2 | 9/2007 | Thiesen |
| 7,309,330 B2 | 12/2007 | Bertrand et al. |
| 7,353,711 B2 | 4/2008 | O'Dowd et al. |
| 7,425,200 B2 | 9/2008 | Brockway et al. |
| 7,432,723 B2 | 10/2008 | Ellis et al. |
| 7,439,723 B2 | 10/2008 | Allen et al. |
| 7,466,120 B2 | 12/2008 | Miller et al. |
| 7,498,799 B2 | 3/2009 | Allen et al. |
| 7,550,978 B2 | 6/2009 | Joy et al. |
| 7,572,228 B2 | 8/2009 | Wolinsky et al. |
| 7,574,492 B2 | 8/2009 | Karaoguz et al. |
| 7,574,792 B2 | 8/2009 | O'Brien et al. |
| 7,595,647 B2 | 9/2009 | Kroh et al. |
| 7,621,036 B2 | 11/2009 | Cros et al. |
| 7,621,878 B2 | 11/2009 | Ericson et al. |
| 7,647,836 B2 | 1/2010 | O'Brien et al. |
| 7,662,653 B2 | 2/2010 | O'Brien et al. |
| 7,679,355 B2 | 3/2010 | Allen et al. |
| 7,699,059 B2 | 4/2010 | Fonseca et al. |
| 7,699,060 B2 | 4/2010 | Behm |
| 7,748,277 B2 | 7/2010 | O'Brien et al. |
| 7,839,153 B2 | 11/2010 | Joy et al. |
| 7,930,032 B2 | 4/2011 | Teske et al. |
| 7,932,732 B2 | 4/2011 | Ellis et al. |
| 7,936,174 B2 | 5/2011 | Ellis et al. |
| 7,973,540 B2 | 7/2011 | Kroh et al. |
| 8,025,625 B2 | 9/2011 | Allen |
| 8,026,692 B2 | 9/2011 | Chang |
| 8,026,729 B2 | 9/2011 | Kroh et al. |
| 8,083,741 B2 | 12/2011 | Morgan et al. |
| 8,140,168 B2 | 3/2012 | Olson et al. |
| 8,237,451 B2 | 8/2012 | Joy et al. |
| 8,278,941 B2 | 10/2012 | Kroh et al. |
| 2001/0001311 A1 | 5/2001 | Park et al. |
| 2002/0013994 A1 | 2/2002 | Ahn |
| 2002/0049394 A1 | 4/2002 | Roy et al. |
| 2002/0052563 A1 | 5/2002 | Penn et al. |
| 2002/0075825 A1 | 6/2002 | Hills et al. |
| 2002/0087059 A1 | 7/2002 | O'keefe |
| 2002/0115920 A1 | 8/2002 | Rich et al. |
| 2002/0138009 A1 | 9/2002 | Brockway et al. |
| 2002/0147416 A1 | 10/2002 | Zogbi |
| 2002/0151816 A1 | 10/2002 | Rich et al. |
| 2002/0170897 A1 | 11/2002 | Hall |
| 2002/0188207 A1 | 12/2002 | Richter |
| 2003/0010808 A1 | 1/2003 | Uhland et al. |
| 2003/0028094 A1 | 2/2003 | Kumar et al. |
| 2003/0031587 A1 | 2/2003 | Hu et al. |
| 2003/0085799 A1 | 5/2003 | Ghabra et al. |
| 2003/0105388 A1 | 6/2003 | Roy et al. |
| 2003/0125790 A1 | 7/2003 | Fastovsky et al. |
| 2003/0136417 A1 | 7/2003 | Fonseca et al. |
| 2003/0139677 A1 | 7/2003 | Fonseca et al. |
| 2003/0143775 A1 | 7/2003 | Brady |
| 2003/0151400 A1 | 8/2003 | Petrovich et al. |
| 2003/0179708 A1 | 9/2003 | Kamerman et al. |
| 2003/0185330 A1 | 10/2003 | Hessel et al. |
| 2003/0219220 A1 | 11/2003 | Ellis et al. |
| 2004/0003285 A1 | 1/2004 | Whelan et al. |
| 2004/0011650 A1 | 1/2004 | Zenhausern et al. |
| 2004/0011659 A1 | 1/2004 | Srinivasan et al. |
| 2004/0017310 A1 | 1/2004 | Vargas-Hurlston et al. |
| 2004/0036626 A1 | 2/2004 | Chan et al. |
| 2004/0057589 A1 | 3/2004 | Pedersen et al. |
| 2004/0059348 A1 | 3/2004 | Geske et al. |
| 2004/0073137 A1 | 4/2004 | Lloyd et al. |
| 2004/0077117 A1 | 4/2004 | Ding et al. |
| 2004/0082851 A1* | 4/2004 | Bilgen et al. ............... 600/424 |
| 2004/0113790 A1 | 6/2004 | Hamel et al. |
| 2004/0118997 A1 | 6/2004 | Lehmann et al. |
| 2004/0122494 A1 | 6/2004 | Eggers et al. |
| 2004/0157367 A1 | 8/2004 | Wong et al. |
| 2004/0176672 A1 | 9/2004 | Silver et al. |
| 2004/0181206 A1 | 9/2004 | Chiu et al. |
| 2004/0211260 A1 | 10/2004 | Girmonsky et al. |
| 2004/0236209 A1 | 11/2004 | Misic et al. |
| 2005/0043670 A1 | 2/2005 | Rosenberg |
| 2005/0046558 A1 | 3/2005 | Buenz et al. |
| 2005/0075697 A1 | 4/2005 | Olson et al. |
| 2005/0085703 A1 | 4/2005 | Behm |
| 2005/0154321 A1 | 7/2005 | Wolinsky et al. |
| 2005/0187482 A1 | 8/2005 | O'Brien et al. |
| 2005/0194174 A1 | 9/2005 | Hipwell et al. |
| 2005/0229710 A1 | 10/2005 | O'Dowd et al. |
| 2006/0025704 A1 | 2/2006 | Stendel et al. |
| 2006/0047327 A1 | 3/2006 | Colvin et al. |

(56) References Cited

U.S. PATENT DOCUMENTS

| | | |
|---|---|---|
| 2006/0052737 A1 | 3/2006 | Bertrand et al. |
| 2006/0052782 A1 | 3/2006 | Morgan et al. |
| 2006/0129056 A1 | 6/2006 | Leuthardt et al. |
| 2006/0174712 A1 | 8/2006 | O'Brien et al. |
| 2006/0177956 A1 | 8/2006 | O'Brien et al. |
| 2006/0178586 A1 | 8/2006 | Dobak |
| 2006/0196277 A1 | 9/2006 | Allen et al. |
| 2006/0235310 A1 | 10/2006 | O'Brien et al. |
| 2006/0241354 A1 | 10/2006 | Allen |
| 2006/0244465 A1 | 11/2006 | Kroh et al. |
| 2006/0283007 A1 | 12/2006 | Cros et al. |
| 2006/0287598 A1 | 12/2006 | Lasater et al. |
| 2006/0287602 A1 | 12/2006 | O'Brien et al. |
| 2006/0287700 A1 | 12/2006 | White et al. |
| 2007/0049845 A1 | 3/2007 | Fleischman et al. |
| 2007/0096715 A1 | 5/2007 | Joy et al. |
| 2007/0100215 A1 | 5/2007 | Powers et al. |
| 2007/0107524 A1 | 5/2007 | O'Brien et al. |
| 2007/0118038 A1 | 5/2007 | Bodecker et al. |
| 2007/0181331 A1 | 8/2007 | Kroh et al. |
| 2007/0185546 A1 | 8/2007 | Tseng et al. |
| 2007/0199385 A1 | 8/2007 | O'Brien et al. |
| 2007/0210786 A1 | 9/2007 | Allen et al. |
| 2007/0222603 A1 | 9/2007 | Lai et al. |
| 2007/0236213 A1 | 10/2007 | Paden et al. |
| 2007/0247138 A1 | 10/2007 | Miller et al. |
| 2007/0261497 A1 | 11/2007 | O'Brien et al. |
| 2007/0276294 A1 | 11/2007 | Gupta et al. |
| 2008/0029590 A1 | 2/2008 | Zosimadis et al. |
| 2008/0060834 A1 | 3/2008 | Eck et al. |
| 2008/0060844 A1 | 3/2008 | Teske et al. |
| 2008/0061955 A1 | 3/2008 | Tang et al. |
| 2008/0077016 A1 | 3/2008 | Sparks et al. |
| 2008/0078567 A1 | 4/2008 | Miller et al. |
| 2008/0081962 A1 | 4/2008 | Miller et al. |
| 2008/0272733 A1 | 11/2008 | Huang |
| 2009/0030291 A1 | 1/2009 | O'Brien et al. |
| 2009/0030397 A1 | 1/2009 | Stofer et al. |
| 2009/0033486 A1 | 2/2009 | Costantino |
| 2009/0033846 A1 | 2/2009 | Yamada et al. |
| 2009/0224773 A1 | 9/2009 | Joy et al. |
| 2009/0224837 A1 | 9/2009 | Joy et al. |
| 2009/0273353 A1 | 11/2009 | Kroh et al. |
| 2009/0278553 A1 | 11/2009 | Kroh et al. |
| 2010/0022896 A1 | 1/2010 | Yadav et al. |
| 2010/0026318 A1 | 2/2010 | Kroh et al. |
| 2010/0058583 A1 | 3/2010 | Cros et al. |
| 2012/0016228 A1 | 1/2012 | Kroh et al. |
| 2014/0084943 A1 | 3/2014 | Kroh et al. |

FOREIGN PATENT DOCUMENTS

| | | |
|---|---|---|
| AU | 2006262234 A1 | 1/2007 |
| AU | 2009201749 A1 | 5/2009 |
| AU | 2009201750 A1 | 5/2009 |
| AU | 2012247061 A1 | 11/2012 |
| AU | 2013263860 A1 | 1/2014 |
| CA | 1158061 A1 | 12/1983 |
| CA | 2539261 A1 | 3/2005 |
| CA | 2613361 A1 | 1/2007 |
| DE | 3330519 A1 | 3/1985 |
| DE | 19510452 A1 | 10/1995 |
| DE | 19644858 A1 | 5/1997 |
| DE | 19853135 A1 | 5/2000 |
| DE | 10052053 A1 | 4/2002 |
| DE | 10135568 A1 | 2/2003 |
| EP | 0072003 A2 | 2/1983 |
| EP | 0337035 A1 | 10/1989 |
| EP | 0450653 A2 | 10/1991 |
| EP | 0646365 A1 | 4/1995 |
| EP | 1491137 A2 | 12/2004 |
| EP | 1677852 A2 | 7/2006 |
| EP | 1817593 A2 | 8/2007 |
| EP | 1893081 A2 | 3/2008 |
| EP | 2090330 A1 | 8/2009 |
| EP | 2265164 A1 | 12/2010 |
| EP | 2268218 A2 | 1/2011 |
| EP | 2456502 A1 | 5/2012 |
| JP | 5870399 | 11/1984 |
| JP | 63171331 | 7/1988 |
| JP | 6481597 | 3/1989 |
| JP | 09259384 | 10/1997 |
| WO | WO-83/03348 A1 | 10/1983 |
| WO | WO-90/06723 A1 | 6/1990 |
| WO | WO-93/08871 A1 | 5/1993 |
| WO | WO-95/33517 A1 | 12/1995 |
| WO | WO-97/09926 A1 | 3/1997 |
| WO | WO-97/11641 A1 | 4/1997 |
| WO | WO-97/32518 A1 | 9/1997 |
| WO | WO-97/32519 A1 | 9/1997 |
| WO | WO-97/33513 A1 | 9/1997 |
| WO | WO-98/47727 A1 | 10/1998 |
| WO | WO-99/34731 A1 | 7/1999 |
| WO | WO-00/16686 A2 | 3/2000 |
| WO | WO-01/00089 A1 | 1/2001 |
| WO | 0135872 A1 | 5/2001 |
| WO | WO-01/87137 A2 | 11/2001 |
| WO | WO-01/97908 A2 | 12/2001 |
| WO | WO-02/058551 A2 | 8/2002 |
| WO | WO-03/032009 A2 | 4/2003 |
| WO | WO-03/061504 A1 | 7/2003 |
| WO | WO-03/106952 A2 | 12/2003 |
| WO | WO-2004/014456 A2 | 2/2004 |
| WO | WO-2004/098701 A1 | 11/2004 |
| WO | WO-2005/019785 A2 | 3/2005 |
| WO | WO-2005/027998 A2 | 3/2005 |
| WO | WO-2006/049796 A2 | 5/2006 |
| WO | WO-2006/086113 A2 | 8/2006 |
| WO | WO-2006/086114 A2 | 8/2006 |
| WO | WO-2006/096582 A1 | 9/2006 |
| WO | WO-2007/002185 A2 | 1/2007 |
| WO | WO-2007/002224 A2 | 1/2007 |
| WO | WO-2007/002225 A2 | 1/2007 |
| WO | WO-2007/008493 A1 | 1/2007 |
| WO | WO-2007/030489 A1 | 3/2007 |
| WO | WO-2007/047571 A2 | 4/2007 |
| WO | WO-2007/047794 A2 | 4/2007 |
| WO | WO-2007/106490 A2 | 9/2007 |
| WO | 2008015679 A2 | 2/2008 |
| WO | WO-2008/031011 A1 | 3/2008 |
| WO | WO-2008/031095 A1 | 3/2008 |
| WO | WO-2008/047727 A1 | 4/2008 |
| WO | WO-2009/146089 A2 | 12/2009 |
| WO | WO-2009/146090 A1 | 12/2009 |
| WO | WO-2011/011104 A1 | 1/2011 |

OTHER PUBLICATIONS

U.S. Appl. No. 13/850,022, Yadav.

"Helix," The American Heritage Dictionary of the English Language. Boston, MA: Houghton Mifflin. Http://www.credoreference.com/entry/7055911 Aug. 21, 2008.

"Interfere," The American Heritage Dictionary of the English Language. Boston, MA: Houghton Mifflin. Http://www.credoreference.com/entry/7072413 Aug. 22, 2008.

"Spiral," The American Heritage Dictionary of the English Language. Boston, MA: Houghton Mifflin. Http://www.credoreference.com/entry/7129585 Aug. 21, 2008.

Adams KR. "Guiding heart failure care by invasive hemodynmaic measurements: possible or useful?" Journal of Cardiac Failure. Apr. 2002, 8(2), pp. 71-73.

Akar O, et al. "A Wireless Batch Sealed Absolute Capacitive Pressure Sensor," Sensor and Actuators. Dec. 15, 2001, 95(1), pp. 29-38.

Akin T, et al. "RF telemetry powering and controlling of hermetically sealed intergrated sensors and actuators," Center for the integrated Sensors and Circuits' Department of Electrical Engineering and Computer Science; University of Michigan; Ann Arbor, Michigan 48109-2122; pp. 145-148.

Akingba G, et al. "An implantable pressure sensor for aneurysmal disease."

Allen, "Micromachined endovascularly implantable wireless aneurysm pressue sensors," International Conference on Solid State Sensors, Actuators and Microsystems, No. 13, pp. 275-278 (2005).

(56) References Cited

OTHER PUBLICATIONS

Baum, R.A., et al. "Aneurysm sac pressure measurements after endovascular repair of abdominal aortic aneurysms," The Journal of Vascular Surgery (Jan. 2001).
Chirlian, "Basic network theory," McGraw Hill Book Co., Impendance section: pp. 275-283, 350-355 (1969).
Chuter T, et al. "Endovascular and surgical techniques," Eur J Vasc Endovasc Surg. Jan. 1997, 13, pp. 85-87.
Collins, "Miniature passive pressure transensor for implanting in the eyes," IEEE Transactions on Biomedical Engineering, vol. 14(2), pp. 74-83 (1967).
Dehennis A and Wise KD, "A double-sided single-chip wireless pressure sensor," Engineering Research Center for Wireless Integrated Microsystems; Department of Electrical Engineering and Computer Science; the University of Michigan, Ann Arbor, MI 48109-2122, US.
Dehennis A and Wise KD, "A Passive-telemetry based pressure sensing system," NSF Engineering Research Center for Wireless Integrated Microsystems; Department of Electrical Engineering and Computer Science; the University of Michigan, Ann Arbor, MI 48109-2122 US.
Farrar JT, et al. "Telemetering of Intraenteric krpessure in man by an externally entergized wireless capsule," Science, New Series. Jun. 18, 1960, 131(3416), pp. 1814.
Fonseca, "High temperature characterization of ceramic pressure sensors," vol. 1, pp. 486-489 (2001).
Gawenda M, et al. "Intra-aneurysm sac pressure—the holy gail of endoluminal grafting of AAA," Eur J Vasc Endovasc Surg. Aug. 2002, 24, pp. 139-145.
Gawenda M, et al. "Pressure is transmitted through PTFE and Dacron Grafts leading the aneurysm sac pressure endoluminal grafting of AAAan in vitro study," Vascular Centre, Iniversity of Cologne, Germany.
George, et al., "Ceramic windows to the future," http://matse1.mse.uiuc.edu/ceramics.html, pp. 1-4 (1995).
Harpster, "A passive wireless integrated humidity sensor," Micro Electro Mechanical Systems, vol. IEEEMEMSCONF, No. 14, pp. 553-557 (2001).
Harris PL and Dimitri S. "Predicting failure of endovascular aneurysm repair," Eur J Vas Endovasc Surg. Jan. 1999, 14, pp. 1-2.
Haynes HE and Witchey AL. "Medical electronics: the pill that talks," DEP, Camden, NJ.
Magalski A, et al. "Continuous ambulatory right heart pressure measurements with an implantable hemodynamic monitor: a multicenter, 12-month follow-up study of patients with chronic heart failure," Journal of Cardiac Failure. Apr. 2002, 8, pp. 63-70.
Manwaring ML, et al. "Remote monitoring of intercranial pressure," Institute of Concology; annals of the Academy of Studencia 4, 2001, pp. 77-80.
Ouriel K. "Role of intrasace pressure measurments after EVAR: can they be followed noninvasively?", Combined Session: Vascular Surgery and interventional Radiology; VII 4.1.
Parodi JC, et al. Intra-eneurysmal pressure after incomplete endovascular exclusion, Journal of Vascular Sergery. Nov. 2001, 24(5), pp. 909-914.
Puers, et al. "Electrodeposited copper indicators for intraocular pressure telemetry; electrodeposited copper inductors for IOP telemetry," Journal of Micromechanics & Microengineering, vol. 10(2), pp. 124-129 (2000).
Schurink GWH, et al. "Endoleakage after stent-graft treatment of abdominal aneurysm: implications on pressure and imaging—an in vitro study," Journal of Vascular Surgery. 28(2), pp. 234-241.
Schurink GWH, et al. "Experimental study of the influence of endoleakage size on pressure i nthe aneurysm sac and the consequences of thrombosis," British Journal of Surgery. 2002, 87, pp. 71-76.
Seifert, et al. "Wirelessly interrogable acoustic sensors," Frequency and Time Form, (Online) No. 4, pp. 1013-1018 (1999).

Shabetai R. Monitoring heart failure hemodynamics with an implanted device: its potential to improve outcome, Journal of the American College of Cardiology. Feb. 19, 2003, 41(4) pp. 575-573.
Sonesson B, et al. "Intra-aneurysm pressure measurements in successfully excluded abdominal aortic aneurysm after endovascular repair," Journal of Vascular Surgery. Apr. 2003, 37(4), pp. 733-738.
Treharne GD, et al. "Quality control during endovascular aneurysm repair: monitoring aneurysmal sac pressure and superficial femoral artery flow velocity," J Endovasc Surg. 1999, 6, pp. 239-245.
Vallabhane S, et al. "Aortic side branch perfusion alone does not account for high intra-sac pressure after endovascular repair (EVAR) in the absence of graft-related endoleak," Royal Liverpool University Hospital, Liverpool, UK.
Zhe J, et al. "A MEMS device for measurement of skin friction with capacitive sensing," Department of Mechanical Engineering, Columbia University, NY 10027; Microelectronics Research Center, New Jersey Institute of Technology, newark, NJ 07102.
Skillern CS, et al. "Endotension in an experimental aneurysm model," Journal of Vascular Surgery. Oct. 2002, 36(4), pp. 814-817.
Notice of Allowance issued Aug. 5, 2011 for U.S. Appl. No. 12/416,904, filed Apr. 1, 2009 and issued as Patent No. 8,026,729 on Sep. 27, 2011 (Inventor—Kroh; Applicant—CardioMEMS; (pp. 1-9).
Issue Notification issued Sep. 27, 2011 for U.S. Appl. No. 12/416,904, filed Apr. 1, 2009 and issued as Patent No. 8,026,729 on Sep. 27, 2011 (Inventor—Kroh; Applicant—CardioMEMS; (pp. 1-1).
Non-Final Office Action issued Mar. 14, 2014 for U.S. Appl. No. 13/245,553, filed Sep. 26, 2011 and published as U.S. 2012/0016228 on Jan. 19, 2012 (Inventor—Kroh; Applicant—CardioMEMS; (pp. 1-12).
International Search Report and Written Opinion issued Nov. 17, 2009 for International Patent Application No. PCT/US2009/039220, which was filed on Apr. 1, 2009 and published as WO 2009/146089 on Dec. 3, 2009 (Inventor —Kroh; Applicant—CardioMEMS; (pp. 1-10).
International Preliminary Report on Patentability issued Oct. 5, 2010 for International Patent Applicantion No. PCT/US2009/039220, which was filed on Apr. 1, 2009 and published as WO 2009/146089 on Dec. 3, 2009 (Inventor—Kroh; Applicant—CardioMEMS; (pp. 1-6).
Restriction Requirement issued Oct. 12, 2011 for U.S. Appl. No. 12/416,916, filed Apr. 1, 2009 and issued as Patent No. 8,278,941 on Oct. 2, 2012 (Inventor—Kroh; Applicant—CardioMEMS; (pp. 1-6).
Response to Restriction Requirement filed Oct. 28, 2011 for U.S. Appl. No. 12/416,916, filed Apr. 1, 2009 and issued as Patent No. 8,278,941 on Oct. 2, 2012 (Inventor—Kroh; Applicant—CardioMEMS; (pp. 1-3).
Ex Parte Quayle Action issued Mar. 15, 2012 for U.S. Appl. No. 12/416,916, filed Apr. 1, 2009 and issued as Patent No. 8,278,941 on Oct. 2, 2012 (Inventor—Kroh; Applicant—CardioMEMS; (pp. 1-5).
Response to Ex Parte Quayle Communication filed May 15, 2012 for U.S. Appl. No. 12/416,916, filed Apr. 1, 2009 and issued as Patent No. 8,278,941 on Oct. 2, 2012 (Inventor—Kroh; Applicant—CardioMEMS; (pp. 1-9).
Notice of Allowance issued May 25, 2012 for U.S. Appl. No. 12/416,916, filed Apr. 1, 2009 and issued as Patent No. 8,278,941 on Oct. 2, 2012 (Inventor—Kroh; Applicant—CardioMEMS; (pp. 1-8).
Issue Notification issued Oct. 2, 2012 for U.S. Appl. No. 12/416,916, filed Apr. 1, 2009 and issued as Patent No. 8,278,941 on Oct. 2, 2012 (Inventor—Kroh; Applicant—CardioMEMS; (pp. 1-1).
Supplemental European Search Report issued Sep. 2, 2013 for European Patent Application No. 09755452.1, which was filed on Apr. 1, 2009 and published as EP 2265164 on Dec. 29, 2010 (Inventor—Kroh; Application—CardioMEMS; (pp. 1-7).
International Search Report and Written Opinion issued Nov. 12, 2009 for International Patent Application No. PCT/US2009/039222, which was filed on Apr. 1, 2009 and published as WO 2009/146090 on Dec. 3, 2009 (Inventor—Kroh; Applicant—CardioMEMS; (pp. 1-5).
International Preliminary Report on Patentability issued Oct. 5, 2010 for International Patent Application No. PCT/US2009/039222,

(56) References Cited

OTHER PUBLICATIONS which was filed on Apr. 1, 2009 and published as WO 2009/146090 on Dec. 3, 2009 (Inventor —Kroh; Applicant—CardioMEMS; (pp. 1-4).

Supplemental European Search Report issued Apr. 29, 2013 for European Patent Application No. 10802580.0, which was filed on May 3, 2010 and published as EP 2456502 on May 30, 2012 (Inventor—Yadev; Applicant—CardioMEMS; (pp. 1-11).

International Search Report and Written Opinion issued Jan. 7, 2011 for International Patent Application No. PCT/US2010/033396, which was filed on May 3, 2010 and published as WO 2011/011104 on Jan. 27, 2011 (Inventor—Yadev; Applicant—CardioMEMS; (pp. 1-7).

International Preliminary Report on Patentability issued Jan. 24, 2012 for International Patent Application No. PCT/US2010/033396, which was filed on May 3, 2010 and published as WO 2011/011104 on Jan. 27, 2011 (Inventor—Yadev; Applicant—CardioMEMS; (pp. 1-5).

Preliminary Amendment filed Nov. 4, 2009 for U.S. Appl. No. 12/612,070, filed Nov. 4, 2009 and published as U.S. 2010/0058583 on Mar. 11, 2010 (Inventor—Cros; Applicant—CardioMEMS; (pp. 1-3).

Restriction Requirement issued Dec. 9, 2010 for U.S. Appl. No. 12/612,070, filed Nov. 4, 2009 and published as U.S. 2010/0058583 on Mar. 11, 2010 (Inventor—Cros; Applicant—CardioMEMS; (pp. 1-6).

Preliminary Amendment and Response to Restriction Requirement filed Jun. 9, 2011 for U.S. Appl. No. 12/612,070, filed Nov. 4, 2009 and published as U.S. 2010/0058583 on Mar. 11, 2010 (Inventor—Cros; Applicant—CardioMEMS; (pp. 1-4).

Non-Final Office Action issued Aug. 26, 2011 for U.S. Appl. No. 12/612,070, which was filed on Nov. 4, 2009 and published as U.S. 2010/0058583 on Mar. 11, 2010 (Inventor—Cros; Applicant—CardioMEMS; (pp. 1-8).

Response to Non-Final Office Action filed Jan. 31, 2012 for U.S. Appl. No. 12/612,070, filed Nov. 4, 2009 and published as U.S. 2010/0058583 on Mar. 11, 2010 (Inventor—Cros; Applicant—CardioMEMS; (pp. 1-13).

Response to Final Office Action filed Jun. 26, 2012 for U.S. Appl. No. 12/612,070, filed Nov. 4, 2009 and published as U.S. 2010/0058583 on Mar. 11, 2010 (Inventor—Cros; Applicant—CardioMEMS; (pp. 1-8).

Non-Final Office Action issued Jul. 18, 2013 for U.S. Appl. No. 12/612,070, filed Nov. 4, 2009 and published as U.S. 2010/0058583 on Mar. 11, 2010 (Inventor—Cros; Applicant—CardioMEMS; (pp. 1-7).

Amendment and Response to Non-Final Office Action filed Jan. 2, 2014 for U.S. Appl. No. 12/612,070, filed Nov. 4, 2009 and published as U.S. 2010/0058583 on Mar. 11, 2010 (Inventor—Cros; Applicant—CardioMEMS; (pp. 1-9).

Non-Final Office Action issued Feb. 24, 2014 for U.S. Appl. No. 12/612,070, which was filed on Nov. 4, 2009 and published as U.S. 2010/0058583 on Mar. 11, 2010 (Inventor—Cros; Applicant—CardioMEMS; (pp. 1-10).

Restriction Requirement issued Jan. 15, 2008 for U.S. Appl. No. 11/204,812, filed Aug. 16, 2005 and issued as Patent No. 7,621,036 on Nov. 24, 2009 (Inventor—Cros; Applicant—CardioMEMS; (pp. 1-7).

Response to Restriction Requirement filed Feb. 15, 2008 for U.S. Appl. No. 11/204,812, filed Aug. 16, 2005 and issued as Patent No. 7,621,036 on Nov. 24, 2009 (Inventor—Cros; Applicant—CardioMEMS; (pp. 1-5).

Restriction Requirement issued Apr. 11, 2008 for U.S. Appl. No. 11/204,812, filed Aug. 16, 2005 and issued as Patent No. 7,621,036 on Nov. 24, 2009 (Inventor—Cros; Applicant—CardioMEMS; (pp. 1-7).

Response to Restriction Requirement filed May 12, 2008 for U.S. Appl. No. 11/204,812, filed Aug. 16, 2005 and issued as Patent No. 7,621,036 on Nov. 24, 2009 (Inventor—Cros; Applicant—CardioMEMS; (pp. 1-5).

Non-Final Office Action issued Jun. 12, 2008 for U.S. Appl. No. 11/204,812, filed Aug. 16, 2005 and issued as Patent No. 7,621,036 on Nov. 24, 2009 (Inventor—Cros; Applicant—CardioMEMS; (pp. 1-7).

Response to Non-Final Office Action filed Dec. 12, 2008 for U.S. Appl. No. 11/204,812, filed Aug. 16, 2005 and issued as Patent No. 7,621,036 on Nov. 24, 2009 (Inventor—Cros; Applicant—CardioMEMS; (pp. 1-15).

Examiner Interview Summary issued Apr. 16, 2009 for U.S. Appl. No. 11/204,812, filed Aug. 16, 2005 and issued as Patent No. 7,621,036 on Nov. 24, 2009 (Inventor—Cros; Applicant—CardioMEMS; (pp. 1-2).

Notice of Allowance issued Jul. 10, 2009 for U.S. Appl. No. 11/204,812, filed Aug. 16, 2005 and issued as Patent No. 7,621,036 on Nov. 24, 2009 (Inventor—Cros; Applicant—CardioMEMS; (pp. 1-4).

Notice of Allowance issued Sep. 29, 2009 for U.S. Appl. No. 11/204,812, filed Aug. 16, 2005 and issued as Patent No. 7,621,036 on Nov. 24, 2009 (Inventor—Cros; Applicant—CardioMEMS; (pp. 1-2).

Examiner Interview Summary issued Oct. 30, 2009 for U.S. Appl. No. 11/204,812, filed Aug. 16, 2005 and issued as Patent No. 7,621,036 on Nov. 24, 2009 (Inventor—Cros; Applicant—CardioMEMS; (pp. 1-3).

Issue Notification issued Nov. 24, 2009 for U.S. Appl. No. 11/204,812, filed Aug. 16, 2005 and issued as Patent No. 7,621,036 on Nov. 24, 2009 (Inventor—Cros; Applicant—CardioMEMS; (pp. 1-1).

Preliminary Amendment filed Jun. 21, 2006 for U.S. Appl. No. 11/157,375, filed Jun. 21, 2005 and published as U.S. 2006/0287602 on Dec. 21, 2006 (Inventor—O'Brien; Applicant—CardioMEMS; (pp. 1-8).

Non-Final Office Action issued Oct. 29, 2007 for U.S. Appl. No. 11/157,375, filed Jun. 21, 2005 and published as U.S. 2006/0287602 on Dec. 21, 2006 (Inventor—O'Brien; Applicant—CardioMEMS; (pp. 1-12).

Response to Non-Final Office Action filed Jan. 29, 2008 for for U.S. Appl. No. 11/157,375, filed Jun. 21, 2005 and published as U.S. 2006/0287602 on Dec. 21, 2006 (Inventor—O'Brien; Applicant—CardioMEMS; (pp. 1-24).

Supplemental Response to Non-Final Office Action filed May 30, 2008 for U.S. Appl. No. 11/157,375, filed Jun. 21, 2005 and published as U.S. 2006/0287602 on Dec. 21, 2006 (Inventor—O'Brien; Applicant—CardioMEMS; (pp. 1-19).

Restriction Requirement issued Aug. 22, 2008 for U.S. Appl. No. 11/157,375, filed Jun. 21, 2005 and published as U.S. 2006/0287602 on Dec. 21, 2006 (Inventor—O'Brien; Applicant—CardioMEMS; (pp. 1-6).

Final Office Action issued Aug. 25, 2008 for U.S. Appl. No. 11/157,375, filed Jun. 21, 2005 and published as U.S. 2006/0287602 on Dec. 21, 2006 (Inventor—O'Brien; Applicant'CardioMEMS; (pp. 1-12).

Response and Amendment to Final Office Action filed Feb. 25, 2009 for U.S. Appl. No. 11/157,375, filed Jun. 21, 2005 and published as U.S. 2006/0287602 on Dec. 21, 2006 (Inventor—O'Brien; Applicant—CardioMEMS; (pp. 1-14).

Non-Final Office Action issued Jun. 1, 2009 for U.S. Appl. No. 11/157,375, filed Jun. 21, 2005 and published as U.S. 2006/0287602 on Dec. 21, 2006 (Inventor—O'Brien; Applicant—CardioMEMS; (pp. 1-11).

Amendment and Response to Non-Final Office Action filed Oct. 23, 2009 for U.S. Appl. No. 11/157,375, filed Jun. 21, 2005 and published as U.S. 2006/0287602 on Dec. 21, 2006 (Inventor—O'Brien; Applicant—CardioMEMS; (pp. 1-11).

Final Office Action issued Jul. 29, 2010 for U.S. Appl. No. 11/157,375, filed Jun. 21, 2005 and published as U.S. 2006/0287602 on Dec. 21, 2006 (Inventor—O'Brien; Applicant—CardioMEMS; (pp. 1-12).

Amendment in Response to Final Office Action filed Jan. 31, 2011 for U.S. Appl. No. 11/157,375, filed Jun. 21, 2005 and published as U.S. 2006/0287602 on Dec. 21, 2006 (Inventor—O'Brien; Applicant—CardioMEMS; (pp. 1-11).

(56) References Cited

OTHER PUBLICATIONS

Non-Final Office Action issued Jan. 16, 2014 for U.S. Appl. No. 11/157,375, filed Jun. 21, 2005 and published as U.S. 2006/0287602 on Dec. 21, 2006 (Inventor—O'Brien; Applicant—CardioMEMS; (pp. 1-11).
International Preliminary Report on Patentability issued Dec. 24, 2007 for International Patent Applicantion No. PCT/US2006/024185, which was filed on Jun. 21, 2006 and published as WO 2007/002225 on Jan. 4, 2007 (Inventor—O'Brien; Applicant—CardioMEMS; (pp. 1-7).
International Search Report and Written Opinion issued Jan. 25, 2007 for International Patent Applicantion No. PCT/US2006/024185, which was filed on Jun. 21, 2006 and published as WO 2007/002225 on Jan. 4, 2007 (Inventor—O'Brien; Applicant—CardioMEMS; (pp. 1-11).
Preliminary Amendment issued Jul. 18, 2008 for U.S. Appl. No. 12/175,803, filed Jul. 18, 2008 and published as U.S. 2009/0030291 on Jan. 29, 2009 (Inventor—O'Brien; Applicant—CardioMEMS; (pp. 1-26).
Restriction Requirement issued Sep. 27, 2011 for U.S. Appl. No. 12/175,803, filed Jul. 18, 2008 and published as U.S. 2009/0030291 on Jan. 29, 2009 (Inventor—O'Brien; Applicant—CardioMEMS; (pp. 1-26).
Response to Restriction Requirement filed Dec. 14, 2011 for U.S. Appl. No. 12/175,803, filed Jul. 18, 2008 and published as U.S. 2009/0030291 on Jan. 29, 2009 (Inventor—O'Brien; Applicant—CardioMEMS; (pp. 1-3).
Non-Final Office Action issued Dec. 20, 2011 for U.S. Appl. No. 12/175,803, filed Jul. 18, 2008 and published as U.S. 2009/0030291 on Jan. 29, 2009 (Inventor—O'Brien; Applicant—CardioMEMS; (pp. 1-12).
Response to Non-Final Office Action filed May 29, 2012 for U.S. Appl. No. 12/175,803, filed Jul. 18, 2008 and published as U.S. 2009/0030291 on Jan. 29, 2009 (Inventor—O'Brien; Applicant—CardioMEMS; (pp. 1-23).
Final Office Action issued Jul. 13, 2012 for U.S. Appl. No. 12/175,803, filed Jul. 18, 2008 and published as U.S. 2009/0030291 on Jan. 29, 2009 (Inventor—O'Brien; Applicant—CardioMEMS; (pp. 1-12).
Response to Final Office Action filed Oct. 13, 2012 for U.S. Appl. No. 12/175,803, filed Jul. 18, 2008 and published as U.S. 2009/0030291 on Jan. 29, 2009 (Inventor—O'Brien; Applicant—CardioMEMS; (pp. 1-11).
Non-Final Office Action issued Apr. 15, 2014 for U.S. Appl. No. 12/175,803, filed Jul. 18, 2008 and published as U.S. 2009/0030291 on Jan. 29, 2009 (Inventor—O'Brien; Applicant—CardioMEMS; (pp. 1-14).
Supplemental European Search Report issued May 27, 2009 for European Patent Application No. 4078884.1, which was filed on Sep. 16, 2004 and published as EP 1677852 on Jul. 12, 2006 (Inventor—O'Brien; Applicant—CardioMEMS; (pp. 1-5).
International Preliminary Report on Patentability issued Oct. 3, 2006 for International Patent Application No. PCT/US2004/030727, which was filed on Sep. 16, 2004 and published as WO 2005/027998 on Mar. 31, 2005 (Inventor—O'Brien; Applicant—CardioMEMS; (pp. 1-9).
International Search Report and Written Opinoin issued Aug. 4, 2006 for International Patent Application No. PCT/US2004/030727, which was filed on Sep. 16, 2004 and published as WO 2005/027998 on Mar. 31, 2005 (Inventor—O'Brien; Applicant—CardioMEMS; (pp. 1-12).
Restriction Requirement issued Jul. 28, 2006 for U.S. Appl. No. 11/105,294, filed Apr. 13, 2005 and issued as U.S. Patent No. 7,245,117 on Jul. 17, 2007 (Inventor—Joy; Applicant—CardioMEMS; (pp. 1-7).
Response to Restriction Requirement filed Aug. 28, 2006 for U.S. Appl. No. 11/105,294, filed Apr. 13, 2005 and issued as U.S. Patent No. 7,245,117 on Jul. 17, 2007 (Inventor—Joy; Applicant—CardioMEMS; (pp. 1-3).
Examiner Interview Summary issued Sep. 20, 2006 for U.S. Appl. No. 11/105,294, filed Apr. 13, 2005 and issued as U.S. Patent No. 7,245,117 on Jul. 17, 2007 (Inventor—Joy; Applicant—CardioMEMS) (pp. 1-1).
Notice of Allowance issued Sep. 20, 2006 for U.S. Appl. No. 11/105,294, filed Apr. 13, 2005 and issued as U.S. Patent No. 7,245,117 on Jul. 17, 2007 (Inventor—Joy; Applicant—CardioMEMS) (pp. 1-6).
Notice of Allowance issued Nov. 6, 2006 for U.S. Appl. No. 11/105,294, filed Apr. 13, 2005 and issued as U.S. Patent No. 7,245,117 on Jul. 17, 2007 (Inventor—Joy; Applicant—CardioMEMS) (pp. 1-2).
Issue Notification issued Jun. 27, 2007 for U.S. Appl. No. 11/105,294, filed Apr. 13, 2005 and issued as U.S. Patent No. 7,245,117 on Jul. 17, 2007 (Inventor—Joy; Applicant—CardioMEMS) (pp. 1-1).
Restriction Requirement issued Jan. 22, 2007 for U.S. Appl. No. 11/479,527, filed Jun. 30, 2006 and issued as U.S. Patent No. 7,432,723 on Oct. 7, 2008 (Inventor—Ellis; Applicant—CardioMEMS) (pp. 1-5).
Response to Restriction Requirement filed Feb. 16, 2007 for U.S. Appl. No. 11/479,527, filed Jun. 30, 2006 and issued as U.S. Patent No. 7,432,723 on Oct. 7, 2008 (Inventor—Ellis; Applicant—CardioMEMS) (pp. 1-6).
Non-Final Office Action issued Mar. 29, 2007 for U.S. Appl. No. 11/479,527, filed Jun. 30, 2006 and issued as U.S. Patent No. 7,432,723 on Oct. 7, 2008 (Inventor—Ellis; Applicant—CardioMEMS) (pp. 1-8).
Examiner Interview Summary issued Jun. 26, 2007 for U.S. Appl. No. 11/479,527, filed Jun. 30, 2006 and issued as U.S. Patent No. 7,432,723 on Oct. 7, 2008 (Inventor—Ellis; Applicant—CardioMEMS) (pp. 1-3).
Amendment and Response filed Jul. 26, 2007 for U.S. Appl. No. 11/479,527, filed Jun. 30, 2006 and issued as U.S. Patent No. 7,432,723 on Oct. 7, 2008 (Inventor—Ellis; Applicant—CardioMEMS) (pp. 1-12).
Notice of Allowance issued Mar. 27, 2008 for U.S. Appl. No. 11/479,527, filed Jun. 30, 2006 and issued as U.S. Patent No. 7,432,723 on Oct. 7, 2008 (Inventor—Ellis; Applicant—CardioMEMS) (pp. 1-9).
Notice of Allowance issued May 23, 2008 for U.S. Appl. No. 11/479,527, filed Jun. 30, 2006 and issued as U.S. Patent No. 7,432,723 on Oct. 7, 2008 (Inventor—Ellis; Applicant—CardioMEMS) (pp. 1-6).
Notice of Allowance issued Aug. 12, 2008 for U.S. Appl. No. 11/479,527, filed Jun. 30, 2006 and issued as U.S. Patent No. 7,432,723 on Oct. 7, 2008 (Inventor—Ellis; Applicant—CardioMEMS) (pp. 1-2).
Issue Notification issued Oct. 7, 2008 for U.S. Appl. No. 11/479,527, filed Jun. 30, 2006 and issued as U.S. Patent No. 7,432,723 on Oct. 7, 2008 (Inventor—Ellis; Applicant—CardioMEMS) (pp. 1-1).
Notice of Allowance issued Aug. 17, 2007 for U.S. Appl. No. 11/748,053, filed May 14, 2007 and issued as U.S. Patent No. 7,439,723 on Oct. 21, 2008 (Inventor—Allen; Applicant—CardioMEMS) (pp. 1-8).
Notice of Allowance issued Jan. 2, 2008 for U.S. Appl. No. 11/748,053, filed May 14, 2007 and issued as U.S. Patent No. 7,439,723 on Oct. 21, 2008 (Inventor—Allen; Applicant—CardioMEMS) (pp. 1-6).
Notice of Allowance issued May 8, 2008 for U.S. Appl. No. 11/748,053, filed May 14, 2007 and issued as U.S. Patent No. 7,439,723 on Oct. 21, 2008 (Inventor—Allen; Applicant—CardioMEMS) (pp. 1-6).
Notice of Allowance issued Aug. 15, 2008 for U.S. Appl. No. 11/748,053, filed May 14, 2007 and issued as U.S. Patent No. 7,439,723 on Oct. 21, 2008 (Inventor—Allen; Applicant—CardioMEMS) (pp. 1-6).
Issue Notification issued Oct. 21, 2008 for U.S. Appl. No. 11/748,053, filed May 14, 2007 and issued as U.S. Patent No. 7,439,723 on Oct. 21, 2008 (Inventor—Allen; Applicant—CardioMEMS) (pp. 1-1).

(56) References Cited

OTHER PUBLICATIONS

Notice of Allowance issued Oct. 2, 2007 for U.S. Appl. No. 11/717,967, filed Mar. 14, 2007 and issued as U.S. Patent No. 7,466,120 on Dec. 16, 2008 (Inventor—Miller; Applicant—CardioMEMS) (pp. 1-7).
Notice of Allowance issued Nov. 21, 2007 for U.S. Appl. No. 11/717,967, filed Mar. 14, 2007 and issued as U.S. Patent No. 7,466,120 on Dec. 16, 2008 (Inventor—Miller; Applicant—CardioMEMS) (pp. 1-2).
Notice of Allowance issued Mar. 31, 2008 for U.S. Appl. No. 11/717,967, filed Mar. 14, 2007 and issued as U.S. Patent No. 7,466,120 on Dec. 16, 2008 (Inventor—Miller; Applicant—CardioMEMS) (pp. 1-6).
Notice of Allowance issued Jul. 14, 2008 for U.S. Appl. No. 11/717,967, filed Mar. 14, 2007 and issued as U.S. Patent No. 7,466,120 on Dec. 16, 2008 (Inventor—Miller; Applicant—CardioMEMS) (pp. 1-6).
Notice of Allowance issued Aug. 21, 2008 for U.S. Appl. No. 11/717,967, filed Mar. 14, 2007 and issued as U.S. Patent No. 7,466,120 on Dec. 16, 2008 (Inventor—Miller; Applicant—CardioMEMS) (pp. 1-6).
Issue Notification issued Nov. 25, 2008 for U.S. Appl. No. 11/717,967, filed Mar. 14, 2007 and issued as U.S. Patent No. 7,466,120 on Dec. 16, 2008 (Inventor—Miller; Applicant—CardioMEMS) (pp. 1-1).
Requirement for Restriction issued Sep. 12, 2008 for U.S. Appl. No. 11/613,645, filed Dec. 20, 2006 and issued as U.S. Patent No. 7,550,978 on Jun. 23, 2009 (Inventor'Kroh; Applicant—CardioMEMS) (pp. 1-5).
Examiner Interview Summary issued Sep. 12, 2008 for U.S. Appl. No. 11/613,645, filed Dec. 20, 2006 and issued as U.S. Patent No. 7,550,978 on Jun. 23, 2009 (Inventor—Kroh; Applicant—CardioMEMS) (pp. 1-2).
Response to Restriction Requirement filed Oct. 14, 2008 for U.S. Appl. No. 11/613,645, filed Dec. 20, 2006 and issued as U.S. Patent No. 7,550,978 on Jun. 23, 2009 (Inventor—Kroh; Applicant—CardioMEMS) (pp. 1-6).
Notice of Allowance issued Dec. 16, 2008 for U.S. Appl. No. 11/613,645, filed Dec. 20, 2006 and issued as U.S. Patent No. 7,550,978 on Jun. 23, 2009 (Inventor—Kroh; Applicant—CardioMEMS) (pp. 1-8).
Notice of Allowance issued Feb. 17, 2009 for U.S. Appl. No. 11/613,645, filed Dec. 20, 2006 and issued as U.S. Patent No. 7,550,978 on Jun. 23, 2009 (Inventor—Kroh; Applicant—CardioMEMS) (pp. 1-6).
Issue Notification issued Jun. 23, 2009 for U.S. Appl. No. 11/613,645, filed Dec. 20, 2006 and issued as U.S. Patent No. 7,550,978 on Jun. 23, 2009 (Inventor—Kroh; Applicant—CardioMEMS) (pp. 1-1).
Non-Final Office Action issued Sep. 8, 2006 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-7).
Response to Non-Final Office Action filed Nov. 8, 2006 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-6).
Final Office Action issued Jan. 25, 2007 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-8).
Response to Final Office Action filed Mar. 19, 2007 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-7).
Advisory Action issued Apr. 16, 2007 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-3).
Pre-Appeal Brief Request for Review filed Apr. 25, 2007 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-6).
Pre-Appeal Brief Conference Decision issued Jul. 2, 2007 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-2).
Response to Final Office Action filed Jan. 25, 2007 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-19).
Non-Final Office Action issued Sep. 20, 2007 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-8).
Response to Non-Final Office Action filed Dec. 7, 2007 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-9).
Final Office Action issued Mar. 21, 2008 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-9).
Response to Final Office Action filed May 8, 2008 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-9).
Advisory Action issued May 30, 2008 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-3).
Non-Final Office Action issued Aug. 6, 2008 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-8).
Response to Non-Final Office Action filed Sep. 24, 2008 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-19).
Final Office Action issued Dec. 17, 2008 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-10).
Response to Final Office Action filed Feb. 17, 2009 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-11).
Advisory Action issued Mar. 9, 2009 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-3).
Non-Final Office Action issued Apr. 14, 2009 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-10).
Response to Non-Final Office Action filed May 18, 2009 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-12).
Notice of Allowance issued Jun. 9, 2009 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-4).
Issue Notification issued Aug. 11, 2009 for U.S. Appl. No. 10/348,894, filed Jan. 23, 2003 and issued as U.S. Patent No. 7,574,492 on Aug. 11, 2009 (Inventor—Karaoguz; Applicant—CardioMEMS) (pp. 1-1).
Non-Final Office Action issued Jun. 12, 2008 for U.S. Appl. No. 11/668,601, filed Jan. 30, 2007 and issued as U.S. Patent No. 7,595,647 on Sep. 29, 2009 (Inventor—Kroh; Applicant—CardioMEMS) (pp. 1-9).

(56) References Cited

OTHER PUBLICATIONS

Amendment and Response to Non-Final Office Action filed Oct. 13, 2008 for U.S. Appl. No. 11/668,601, filed Jan. 30, 2007 and issued as U.S. Patent No. 7,595,647 on Sep. 29, 2009 (Inventor—Kroh; Applicant—CardioMEMS) (pp. 1-12).

Final Office Action issued Jan. 6, 2009 for U.S. Appl. No. 11/668,601, filed Jan. 30, 2007 and issued as U.S. Patent No. 7,595,647 on Sep. 29, 2009 (Inventor—Kroh; Applicant—CardioMEMS) (pp. 1-13).

Amendment and Response to Final Office Action May 1, 2009 for U.S. Appl. No. 11/668,601, filed Jan. 30, 2007 and issued as U.S. Patent No. 7,595,647 on Sep. 29, 2009 (Inventor—Kroh; Applicant—CardioMEMS) (pp. 1-9).

Notice of Allowance issued Jun. 1, 2009 for U.S. Appl. No. 11/668,601, filed Jan. 30, 2007 and issued as U.S. Patent No. 7,595,647 on Sep. 29, 2009 (Inventor—Kroh; Applicant—CardioMEMS) (pp. 1-7).

Issue Notification issued Sep. 9, 2009 for U.S. Appl. No. 11/668,601, filed Jan. 30, 2007 and issued as U.S. Patent No. 7,595,647 on Sep. 29, 2009 (Inventor—Kroh; Applicant—CardioMEMS) (pp. 1-1).

Non-Final Office Action issued Jun. 24, 2009 for U.S. Appl. No. 12/349,606, filed Jan. 7, 2009 and issued as U.S. Patent No. 7,679,355 on Mar. 16, 2010 (Inventor—Allen; Applicant—CardioMEMS) (pp. 1-7).

Examiner Interview Summary issued Aug. 25, 2009 for U.S. Appl. No. 12/349,606, filed Jan. 7, 2009 and issued as U.S. Patent No. 7,679,355 on Mar. 16, 2010 (Inventor—Allen; Applicant—CardioMEMS) (pp. 1-2).

Amendment and Response for Non-Final Office Action filed Sep. 24, 2009 for U.S. Appl. No. 12/349,606, filed Jan. 7, 2009 and issued as U.S. Patent No. 7,679,355 on Mar. 16, 2010 (Inventor—Allen; Applicant—CardioMEMS) (pp. 1-9).

Notice of Allowance issued Dec. 15, 2009 for U.S. Appl. No. 12/349,606, filed Jan. 7, 2009 and issued as U.S. Patent No. 7,679,355 on Mar. 16, 2010 (Inventor—Allen; Applicant—CardioMEMS) (pp. 1-4).

Notice of Allowance issued Feb. 4, 2010 for U.S. Appl. No. 12/349,606, filed Jan. 7, 2009 and issued as U.S. Patent No. 7,679,355 on Mar. 16, 2010 (Inventor—Allen; Applicant—CardioMEMS) (pp. 1-2).

Issue Notification issued Feb. 24, 2010 for U.S. Appl. No. 12/349,606, filed Jan. 7, 2009 and issued as U.S. Patent No. 7,679,355 on Mar. 16, 2010 (Inventor—Allen; Applicant—CardioMEMS) (pp. 1-1).

Non-Final Office Action issued Mar. 24, 2010 for U.S. Appl. No. 12/466,541, filed May 15, 2009 and issued as U.S. Patent No. 7,839,153 on Nov. 23, 2010 (Inventor—Joy; Applicant—CardioMEMS) (pp. 1-8).

Examiner Interview Summary issued Jun. 21, 2010 for U.S. Appl. No. 12/466,541, filed May 15, 2009 and issued as U.S. Patent No. 7,839,153 on Nov. 23, 2010 (Inventor—Joy; Applicant—CardioMEMS) (pp. 1-4).

Amendment and Response for Non-Final Office Action filed Jun. 24, 2010 for U.S. Appl. No. 12/466,541, filed May 15, 2009 and issued as U.S. Patent No. 7,839,153 on Nov. 23, 2010 (Inventor—Joy; Applicant—CardioMEMS) (pp. 1-10).

Terminal Disclaimer filed Jun. 24, 2010 for U.S. Appl. No. 12/466,541, filed May 15, 2009 and issued as U.S. Patent No. 7,839,153 on Nov. 23, 2010 (Inventor—Joy; Applicant—CardioMEMS) (pp. 1-1).

Terminal Disclaimer Review Decision issued Jul. 6, 2010 for U.S. Appl. No. 12/466,541, filed May 15, 2009 and issued as U.S. Patent No. 7,839,153 on Nov. 23, 2010 (Inventor—Joy; Applicant—CardioMEMS) (pp. 1-1).

Notice of Allowance issued Aug. 25, 2010 for U.S. Appl. No. 12/466,541, filed May 15, 2009 and issued as U.S. Patent No. 7,839,153 on Nov. 23, 2010 (Inventor—Joy; Applicant—CardioMEMS) (pp. 1-6).

Issue Notification issued Nov. 3, 2010 for U.S. Appl. No. 12/466,541, filed May 15, 2009 and issued as U.S. Patent No. 7,839,153 on Nov. 23, 2010 (Inventor—Joy; Applicant—CardioMEMS) (pp. 1-1).

Non-Final Office Action issued Oct. 15, 2010 for U.S. Appl. No. 12/466,595, filed May 15, 2009 and issued as U.S. Patent No. 7,932,732 on Apr. 26, 2011 (Inventor—Kroh; Applicant—CardioMEMS) (pp. 1-6).

Amendment and Response for Non-Final Office Action filed Dec. 10, 2010 for U.S. Appl. No. 12/466,595, filed May 15, 2009 and issued as U.S. Patent No. 7,932,732 on Apr. 26, 2011 (Inventor—Kroh; Applicant—CardioMEMS) (pp. 1-8).

Notice of Allowance issued Dec. 29, 2010 for U.S. Appl. No. 12/466,595, filed May 15, 2009 and issued as U.S. Patent No. 7,932,732 on Apr. 26, 2011 (Inventor—Kroh; Applicant—CardioMEMS) (pp. 1-4).

Issue Notification issued Apr. 6, 2011 for U.S. Appl. No. 12/466,595, filed May 15, 2009 and issued as U.S. Patent No. 7,932,732 on Apr. 26, 2011 (Inventor—Kroh; Applicant—CardioMEMS) (pp. 1-1).

Preliminary Amendment filed Oct. 16, 2009 for U.S. Appl. No. 12/545,166, filed Aug. 21, 2009 and issued as U.S. Patent No. 7,936,174 on May 3, 2011 (Inventor—Kroh; Applicant—CardioMEMS) (pp. 1-3).

Non-Final Office Action issued Jun. 25, 2010 for U.S. Appl. No. 12/545,166, filed Aug. 21, 2009 and issued as U.S. Patent No. 7,936,174 on May 3, 2011 (Inventor—Kroh; Applicant—CardioMEMS) (pp. 1-7).

Terminal Disclaimer filed Oct. 7, 2010 for U.S. Appl. No. 12/545,166, filed Aug. 21, 2009 and issued as U.S. Patent No. 7,936,174 on May 3, 2011 (Inventor—Kroh; Applicant—CardioMEMS) (pp. 1-2).

Response to Non-Final Office Action filed Oct. 7, 2010 for U.S. Appl. No. 12/545,166, filed Aug. 21, 2009 and issued as U.S. Patent No. 7,936,174 on May 3, 2011 (Inventor—Kroh; Applicant—CardioMEMS) (pp. 1-7).

Examiner Interview Summary issued Oct. 12, 2010 for U.S. Appl. No. 12/545,166, filed Aug. 21, 2009 and issued as U.S. Patent No. 7,936,174 on May 3, 2011 (Inventor—Kroh; Applicant—CardioMEMS) (pp. 1-4).

Terminal Disclaimer Review Decision issued Oct. 31, 2010 for U.S. Appl. No. 12/545,166, filed Aug. 21, 2009 and issued as U.S. Patent No. 7,936,174 on May 3, 2011 (Inventor—Kroh; Applicant—CardioMEMS) (pp. 1-1).

Notice of Allowance issued Dec. 23, 2010 for U.S. Appl. No. 12/545,166, filed Aug. 21, 2009 and issued as U.S. Patent No. 7,936,174 on May 3, 2011 (Inventor—Kroh; Applicant—CardioMEMS) (pp. 1-7).

Issue Notification issued Apr. 13, 2011 for U.S. Appl. No. 12/545,166, filed Aug. 21, 2009 and issued as U.S. Patent No. 7,936,174 on May 3, 2011 (Inventor—Kroh; Applicant—CardioMEMS) (pp. 1-1).

Notice of Allowance issued Mar. 18, 2011 for U.S. Appl. No. 12/765,970, filed Apr. 23, 2010 and issued as U.S. Patent No. 7,973,540 on Jul. 5, 2011 (Inventor—Kroh; Applicant—CardioMEMS) (pp. 1-8).

Amendment After Notice of Allowance May 24, 2011 for U.S. Appl. No. 12/765,970, filed Apr. 23, 2010 and issued as U.S. Patent No. 7,973,540 on Jul. 5, 2011 (Inventor—Kroh; Applicant—CardioMEMS) (pp. 1-5).

Issue Notification issued Jun. 15, 2011 for U.S. Appl. No. 12/765,970, filed Apr. 23, 2010 and issued as U.S. Patent No. 7,973,540 on Jul. 5, 2011 (Inventor—Kroh; Applicant—CardioMEMS) (pp. 1-1).

Non-Final Office Action issued Dec. 8, 2011 for U.S. Appl. No. 13/078,091, filed Apr. 1, 2011 and issued as U.S. Patent No. 8,237,451 on Aug. 7, 2012 (Inventor—Joy; Applicant—CardioMEMS) (pp. 1-7).

Applicant-Initiated Interview Summary issued Mar. 6, 2012 for U.S. Appl. No. 13/078,091, filed Apr. 1, 2011 and issued as U.S. Patent No. 8,237,451 on Aug. 7, 2012 (Inventor—Joy; Applicant—CardioMEMS) (pp. 1-3).

(56) References Cited

OTHER PUBLICATIONS

Response to Non-Final Office Action issued Mar. 8, 2012 for U.S. Appl. No. 13/078,091, filed Apr. 1, 2011 and issued as U.S. Patent No. 8,237,451 on Aug. 7, 2012 (Inventor—Joy; Applicant—CardioMEMS) (pp. 1-10).
Notice of Allowance issued Apr. 4, 2012 for U.S. Appl. No. 13/078,091, filed Apr. 1, 2011 and issued as U.S. Patent No. 8,237,451 on Aug. 7, 2012 (Inventor—Joy; Applicant—CardioMEMS) (pp. 1-7).
Notice of Allowance issued May 17, 2012 for U.S. Appl. No. 13/078,091, filed Apr. 1, 2011 and issued as U.S. Patent No. 8,237,451 on Aug. 7, 2012 (Inventor—Joy; Applicant—CardioMEMS) (pp. 1-2).
Issue Notification issued Jul. 18, 2012 for U.S. Appl. No. 13/078,091, filed Apr. 1, 2011 and issued as U.S. Patent No. 8,237,451 on Aug. 7, 2012 (Inventor—Joy; Applicant—CardioMEMS) (pp. 1-1).
Non-Final Office Action issued Jun. 9, 2006 for U.S. Appl. No. 10/943,772, filed Sep. 16, 2004 and published as U.S. 2005/0187482 on Aug. 25, 2005 (Inventor—O'Brien; Applicant—CardioMEMS) (pp. 1-15).
Amendment and Response to Non-Final Office Action filed Oct. 13, 2006 for U.S. Appl. No. 10/943,772, filed Sep. 16, 2004 and published as U.S. 2005/0187482 on Aug. 25, 2005 (Inventor—O'Brien; Applicant—CardioMEMS) (pp. 1-34).
Final Office Action issued Mar. 7, 2007 for U.S. Appl. No. 10/943,772, filed Sep. 16, 2004 and published as U.S. 2005/0187482 on Aug. 25, 2005 (Inventor—O'Brien; Applicant—CardioMEMS) (pp. 1-19).
Notice of Abandonment issued Oct. 1, 2007 for U.S. Appl. No. 10/943,772, filed Sep. 16, 2004 and published as U.S. 2005/0187482 on Aug. 25, 2005 (Inventor—O'Brien; Applicant—CardioMEMS) (pp. 1-2).
Preliminary Amendment filed Jun. 21, 2006 for U.S. Appl. No. 11/232,534, filed Sep. 22, 2005 and published as U.S. 2006/0287700 on Dec. 21, 2006 (Inventor—White; Applicant—CardioMEMS) (pp. 1-4).
Non-Final Office Action issued Oct. 18, 2008 for U.S. Appl. No. 11/232,534, filed Sep. 22, 2005 and published as U.S. 2006/0287700 on Dec. 21, 2006 (Inventor—White; Applicant—CardioMEMS) (pp. 1-11).
Response to Non-Final Office Action filed Apr. 15, 2009 for U.S. Appl. No. 11/232,534, filed Sep. 22, 2005 and published as U.S. 2006/0287700 on Dec. 21, 2006 (Inventor—White; Applicant—CardioMEMS) (pp. 1-15).
Final Office Action issued Jul. 10, 2009 for U.S. Appl. No. 11/232,534, filed Sep. 22, 2005 and published as U.S. 2006/0287700 on Dec. 21, 2006 (Inventor—White; Applicant—CardioMEMS) (pp. 1-12).
Notice of Abandonment issued Feb. 16, 2010 for U.S. Appl. No. 11/232,534, filed Sep. 22, 2005 and published as U.S. 2006/0287700 on Dec. 21, 2006 (Inventor—White; Applicant—CardioMEMS) (pp. 1-2).
International Search Report issued Jul. 28, 2006 for International Patent Application No. PCT/US2006/007790, which was filed on Mar. 6, 2006 and published as WO 2006/096582 on Sep. 14, 2006 (Inventor—Allen; Applicant —CardioMEMS) (pp. 1-3).
Supplementary European Search Report issued Feb. 1, 2012 for EP Patent Application No. 05805691.2, which was filed on Oct. 4, 2005 and published as EP 1817593 on Aug. 15, 2007 (Inventor—James; Applicant—CardioMEMS) (pp. 1-7).
Final Office Action issued Mar. 26, 2012 for U.S. Appl. No. 12/612,070, filed Nov. 4, 2009 and published as U.S. 2010/0058583 on Mar. 11, 2010 (Inventor—Cros; Applicant—CardioMEMS) (pp. 1-8).
Notice of Allowance issued Mar. 23, 2009 for U.S. Appl. No. 11/204,812, filed Aug. 16, 2005 and issued as Patent No. 7,621,036 on Nov. 24, 2009 (Inventor—Cros; Applicant—CardioMEMS) (pp. 1-7).

Requirement for Restriction issued May 10, 2012 for U.S. Appl. No. 12/509,053, filed Jul. 24, 2009 and published as U.S. 2010/0022896 on Jan. 28, 2010 (Inventor—Yadav; Applicant—CardioMEMS) (pp. 1-7).
Response to Restriction Requirement filed May 17, 2012 for U.S. Appl. No. 12/509,053, filed Jul. 24, 2009 and published as U.S. 2010/0022896 on Jan. 28, 2010 (Inventor—Yadav; Applicant—CardioMEMS) (pp. 1-3).
Non-Final Office Action issued Aug. 2, 2012 for U.S. Appl. No. 12/509,053, filed Jul. 24, 2009 and published as U.S. 2010/0022896 on Jan. 28, 2010 (Inventor—Yadav; Applicant—CardioMEMS) (pp. 1-13).
Response to Non-Final Office Action filed Feb. 4, 2014 for U.S. Appl. No. 12/509,053, filed Jul. 24, 2009 and published as U.S. 2010/0022896 on Jan. 28, 2010 (Inventor—Yadav; Applicant—CardioMEMS) (pp. 1-18).
Final Office Action issued Jun. 3, 2013 for U.S. Appl. No. 12/509,053, filed Jul. 24, 2009 and published as U.S. 2010/0022896 on Jan. 28, 2010 (Inventor—Yadav; Applicant—CardioMEMS) (pp. 1-6).
Response to Final Office Action filed Dec. 2, 2013 for U.S. Appl. No. 12/509,053, filed Jul. 24, 2009 and published as U.S. 2010/0022896 on Jan. 28, 2010 (Inventor—Yadav; Applicant—CardioMEMS) (pp. 1-12).
Requirement for Restriction issued Dec. 12, 2006 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-7).
Response to Restriction Requirement filed Jan. 10, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-5).
Notice of Allowance issued Feb. 14, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-3).
Request for Continued Examination filed May 14, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-1).
Notice of Allowance issued Jun. 18, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-2).
Examiner Interview Summary issued Jul. 23, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-2).
Notice of Allowance issued Jul. 23, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-3).
Request for Continued Examination filed Oct. 23, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-1).
Notice of Allowance issued Nov. 21, 2007 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-3).
Request for Continued Examination filed Feb. 21, 2008 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-3).
Notice of Allowance issued Mar. 5, 2008 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-6).

(56) References Cited

OTHER PUBLICATIONS

Request for Continued Examination filed Jun. 5, 2008 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-3).

Notice of Allowance issued Jun. 13, 2008 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-6).

Request for Continued Examination filed Sep. 10, 2008 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-3).

Notice of Allowance issued Oct. 7, 2008 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-6).

Issue Notification issued Feb. 11, 2009 for U.S. Appl. No. 11/276,571, filed Mar. 6, 2006 and issued as U.S. Patent 7,498,799 on Mar. 3, 2009 (Inventor—Allen; Applicant—CardioMEMS) (pp. 1-1).

* cited by examiner

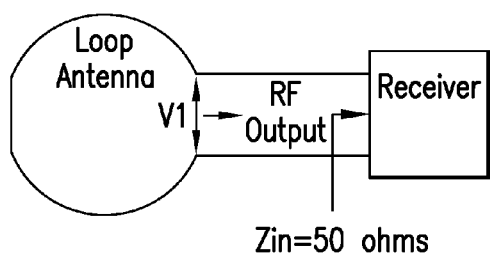
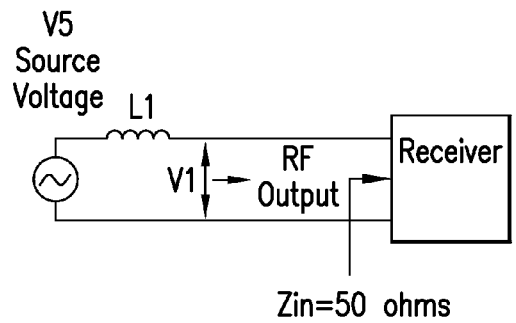
FIG.17A  FIG.17B
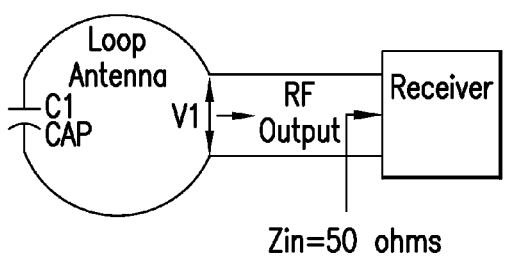
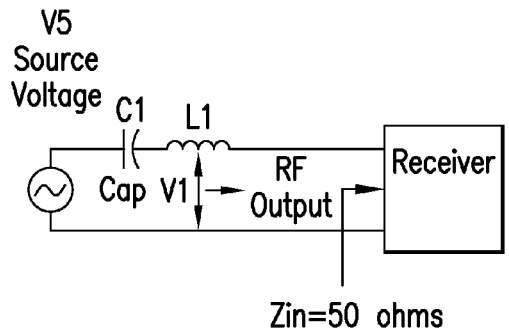
FIG.18A  FIG.18B
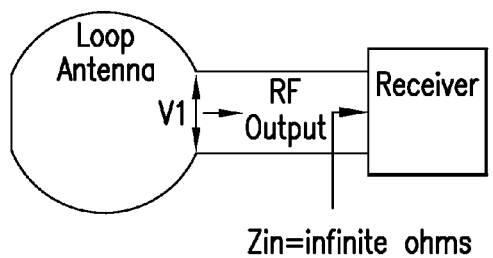
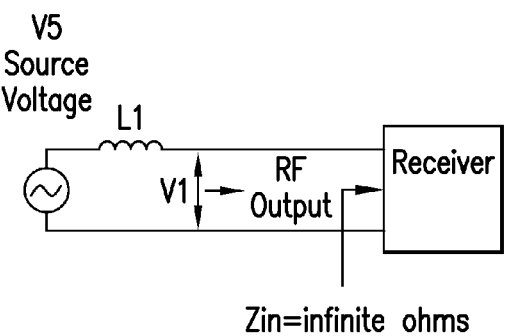
FIG.19A  FIG.19B

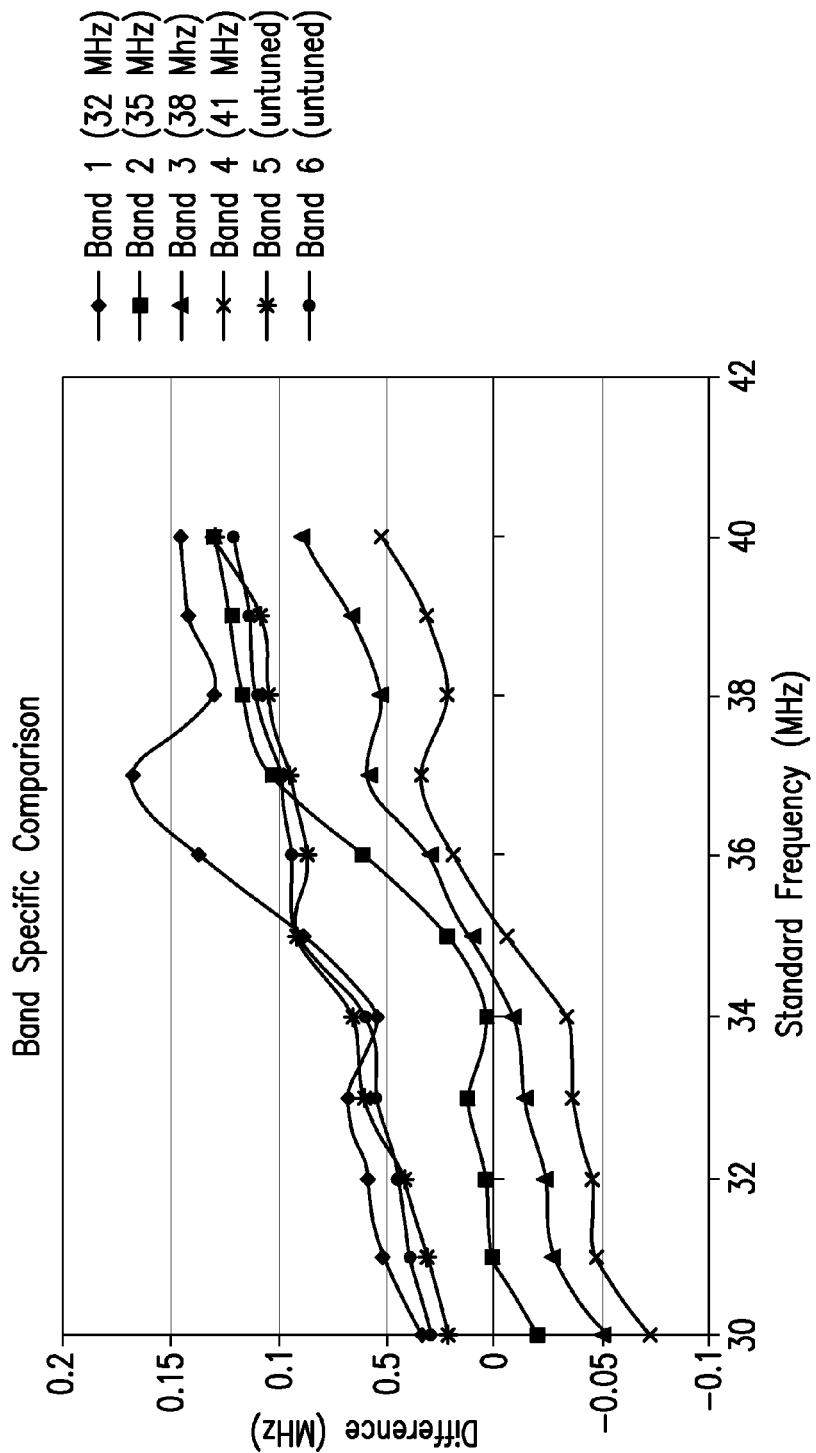

SYSTEM, APPARATUS, AND METHOD FOR IN-VIVO ASSESSMENT OF RELATIVE POSITION OF AN IMPLANT

This application is a continuation application of U.S. patent application Ser. No. 12/416,904, filed Sep. 27, 2011, which is a continuation-in-part of U.S. patent application Ser. No. 11/613,645, filed on Dec. 20, 2006, which is a continuation of U.S. patent application Ser. No. 11/105,294, filed on Apr. 13, 2005, now U.S. Pat. No. 7,245,117, which claims priority to U.S. Provisional Application No. 60/623,959, filed on Nov. 1, 2004. This application is also a continuation-in-part of U.S. patent application Ser. No. 11/717,967, filed on Mar. 14, 2007, now U.S. Pat. No. 7,466,120, which is a continuation-in-part of U.S. patent application Ser. No. 11/276,571, filed on Mar. 6, 2006, now U.S. Pat. No. 7,498,799 which is a continuation-in-part of U.S. patent application Ser. No. 11/105,294, filed on Apr. 13, 2005, now U.S. Pat. No. 7,245,117, which claims priority to U.S. Provisional Application No. 60/623,959, filed on Nov. 1, 2004. U.S. patent application Ser. No. 11/717,967 also claims priority to U.S. Provisional Application No. 60/782,313, filed on Mar. 14, 2006. Further, this application is a continuation-in-part of U.S. patent application Ser. No. 12/175,803, filed on Jul. 18, 2008, which is a divisional of U.S. patent application Ser. No. 11/472,905, filed on Jun. 22, 2006, which is a divisional of U.S. patent application Ser. No. 10/943,772, filed on Sep. 16, 2004, which claims priority to U.S. Provisional Application No. 60/503,745, filed on Sep. 16, 2003. Additionally, this application is a continuation-in-part of U.S. patent application Ser. No. 11/157,375, filed on Jun. 21, 2005. This application also claims priority to U.S. Provisional Application No. 61/072,715, filed on Apr. 1, 2008.

BACKGROUND OF THE INVENTION

1. Field of the Invention

The present invention generally relates to systems, apparatus and methods for determining a relative position of at least a portion of an implant within a living being, and more particularly, to systems and apparatus for determining at least one positional variable of the implant of choice.

2. Background Art

Implants, such as prosthetic implants, are often subject to forces over their implant life times that can cause at least a portion of the implant to move relative to the desired implant position. Often, the undesired movement of the implant can cause undue wear on the implant, potential failure of the implant, and limitations on the mobility of the patient. This undesired implant movement ultimately can cause the patient to undergo a revision or replacement implant surgery, which, in addition to the normal surgical risks, may not necessarily allow for the degree of mobility that the original implant afforded due to scar tissue formation and other surgical limitations that could be inherent to the particular implantation site.

The system, apparatus and methods of embodiments described herein overcome at least the above-described disadvantages by providing an ability to accurately and non-invasively monitor the relative position of an implant positioned within the living being. As one will appreciate, it is desirable to gather information relating to the relative position of the implant in order to monitor the structural viability of the implant; to characterize the mechanical behavior of implant materials and structures under loading conditions; and to detect early sign of catastrophic failure events. Further, it is desirable to monitor the precise relative position of the implant within the living being non-invasively.

Exemplary biomedical applications of the relative position analysis described herein, without limitation, include its use in acute monitoring applications, such as, for example and without limitation, total disk replacement procedures and total knee replacement procedures and chronic monitoring applications.

For example, a total disk replacement procedure is typically recommended when the native disk is not able to perform its function as a cushion between two vertebrae. The total disk replacement procedure replaces the native disk and with a disk implant that is configured to restore appropriate spacing between adjoining vertebrae. Referring to FIG. 1, typically, a conventional artificial disk implant comprises end portions 6 that are configured to contact the bone and, in some case, provide a temporary or permanent anchoring of the artificial disk implant onto one or both vertebrae 1, 2 that under or overlie the native disk. Conventionally, the anchoring of the disk implant is achieved via mechanical fasteners, such as screws 11, biocompatible cements, and the like. Conventionally, the disk implant also has pliant section 8 that is interposed between the end portions and that is configured to emulate the function of the original disk. The pliant section should, at least in theory, be able to absorb shocks and allow motion to occur between the two adjoining vertebrae while maintaining desired alignment. The degrees of freedom as well as the amplitude of the tolerated motion are dictated by design, choice of material, etc. It is beneficial to the surgeon performing the disk replacement surgery to know the precise distance measurements between various portions of the implant prosthesis and/or between portions of the implant prosthesis and the adjoining tissues, such as, for example, bone tissue, both during the replacement surgery and in the days, months, and years after the implantation of the implant prosthesis.

SUMMARY

This application relates to an apparatus and methods for providing an in-vivo assessment of relative movement of an implant that is positioned in a living being. In one aspect, the apparatus comprises a first assembly and a second assembly that are positioned within the living being. In one aspect, the first assembly comprises a passive electrical resonant circuit that is configured to be selectively electromagnetically coupled to an ex-vivo source of radio frequency ("RF") energy and, in response to the electromagnetic coupling, to generate an output resonant frequency that is dependent upon a distance between the first assembly and the second assembly at the time of the electromagnetic coupling.

In one aspect, it is contemplated that the passive electrical resonant circuit of the first assembly comprises an inductive-capacitance ("LC") resonant circuit. It is also contemplated that the second assembly can be optionally selected from a metallic element, a non-metallic element that is at least partially magnetic, and a passive electrical circuit. In a further aspect, if a passive electrical circuit is used in the second assembly, it is contemplated that a LC resonant circuit can be used.

In operation, at a first predetermined distance between the first assembly and the second assembly, the first assembly can be configured to generate a first output resonant frequency in response to the electromagnetic coupling, and wherein, at a distance between the first assembly and the second assembly that differs from the first predetermined distance, the first assembly will generate an output resonant frequency in response to the electromagnetic coupling that differs from the first output resonant frequency.

DETAILED DESCRIPTION OF THE FIGURES

These and other features of the preferred embodiments of the invention will become more apparent in the detailed description in which reference is made to the appended drawings wherein.

Figure 1:
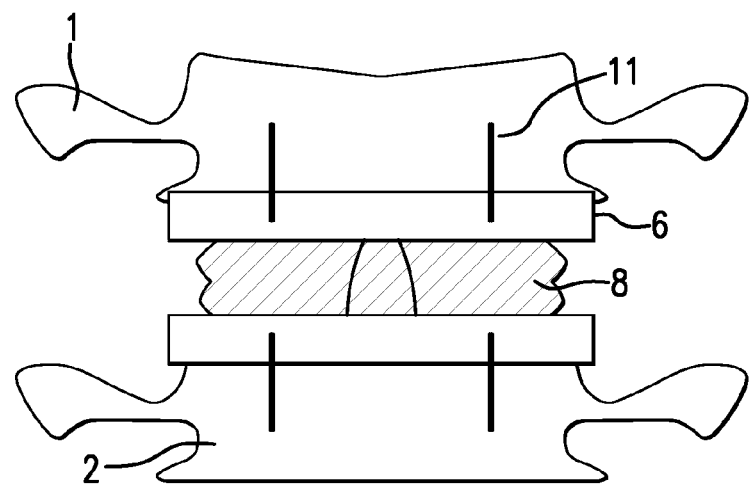
FIG. 1 is a schematic showing an exemplary conventional implant disposed therebetween adjoining vertebrae and secured with conventional pedicle screw fasteners.
Figure 2:
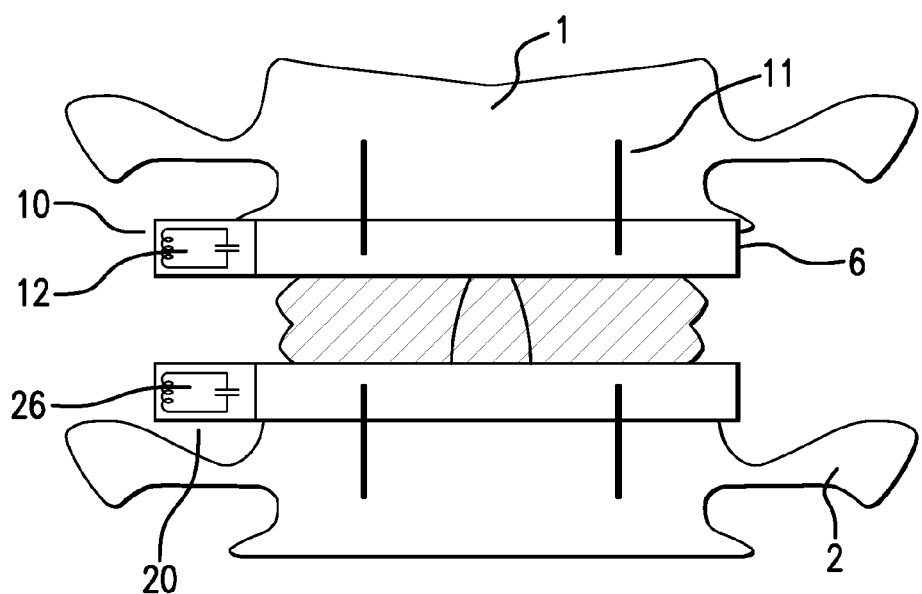
FIG. 2 is a schematic showing a first assembly and a second assembly mounted thereon respective spaced portions of an implant, the first and second assemblies both comprising electrical resonant circuits.
Figure 3:
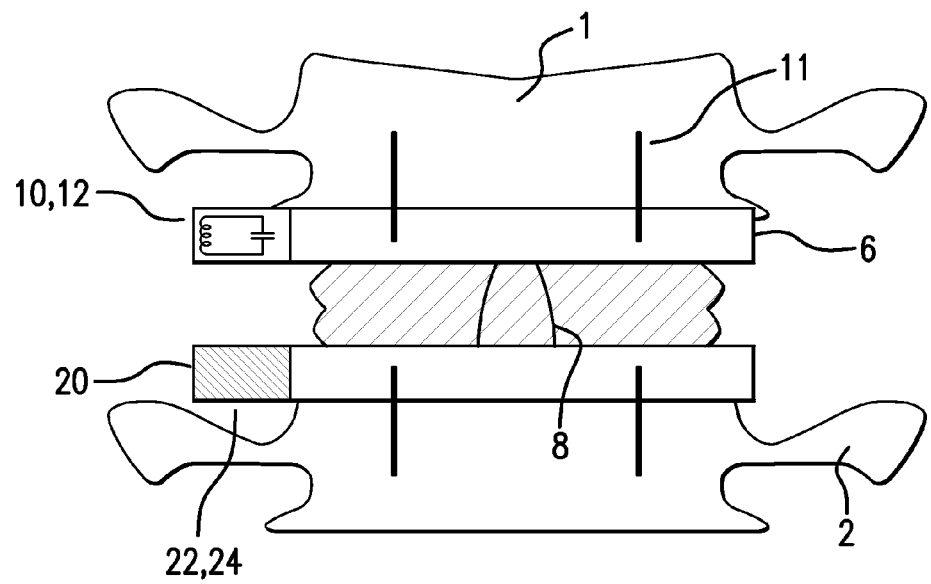
FIG. 3 is a schematic showing a first assembly and a second assembly mounted thereon respective spaced portions of an implant, the first assembly comprising an electrical resonant circuit and the second assembly comprising a metallic or non-metallic element.
Figure 4:
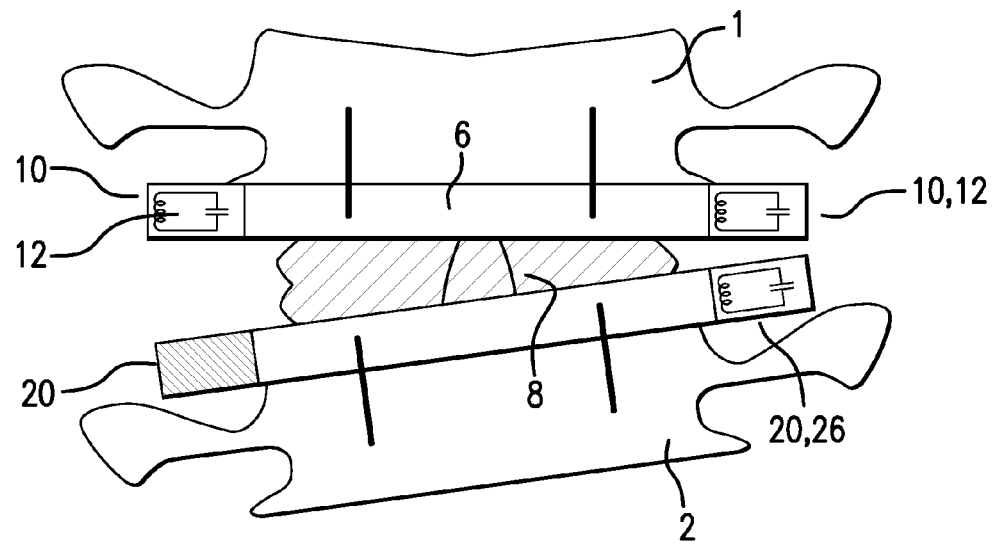

FIG. 4 is a schematic showing a plurality of first assemblies and a plurality of second assemblies mounted thereon respective spaced portions of an implant, in one example showing a pair of opposed first and second assemblies that both comprise electrical resonant circuits and a second pair of opposed first and second assemblies in which the first assembly comprising an electrical resonant circuit and the second assembly comprising a metallic or non-metallic element.

Figure 5:
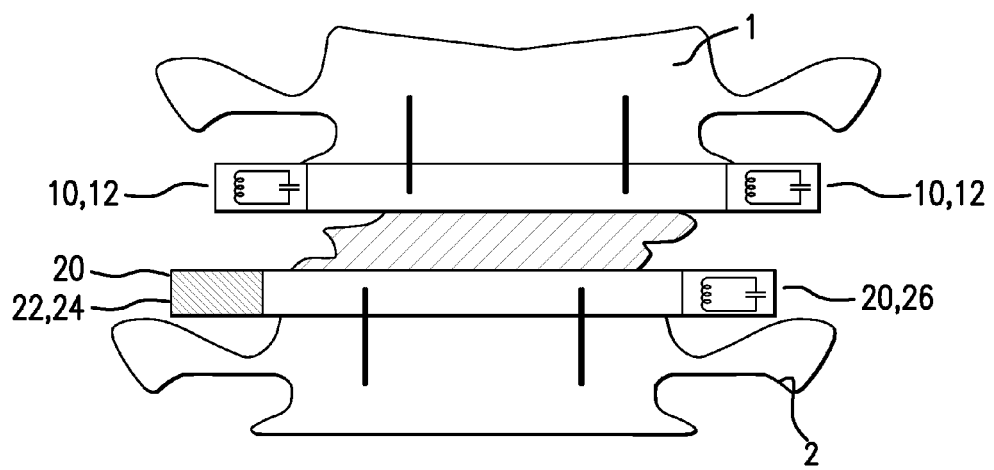

FIG. 5 is a schematic showing the implant of FIG. 4 with portions of the implant offset from the longitudinal axis of the implant.

Figure 6:
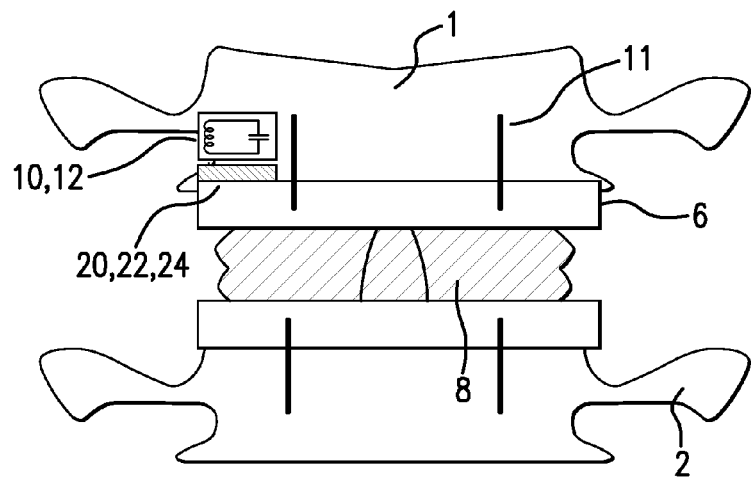

FIG. 6 is a schematic showing a first assembly mounted therein a portion of the bone tissue of the vertebrae and a spaced second assembly mounted thereon a portion of an implant, the first assembly comprising an electrical resonant circuit and the second assembly comprising a metallic or non-metallic element.

Figure 7:
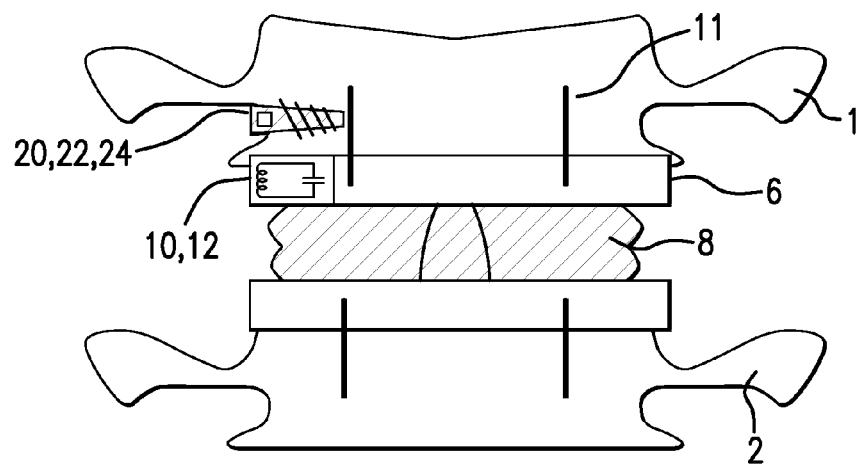

FIG. 7 is a schematic showing a first assembly mounted thereon a portion of an implant and a spaced second assembly mounted therein a portion of the bone tissue of the vertebrae, the first assembly comprising an electrical resonant circuit and the second assembly comprising a metallic or non-metallic element.

Figure 8:
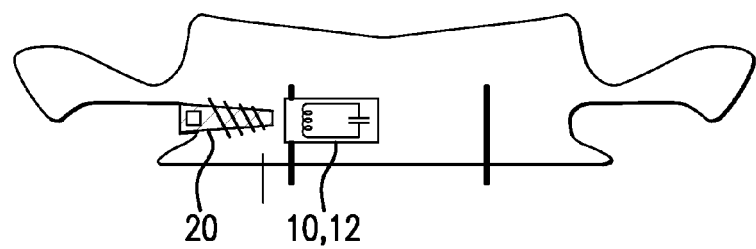

FIG. 8 is a schematic showing a first assembly mounted therein a portion of a bore within the bone tissue of the vertebrae, the first assembly being positioned below and spaced from an exemplary fastener which can serve as a second assembly, the first assembly comprising an electrical resonant circuit and the second assembly comprising a metallic or non-metallic element.

Figure 9:
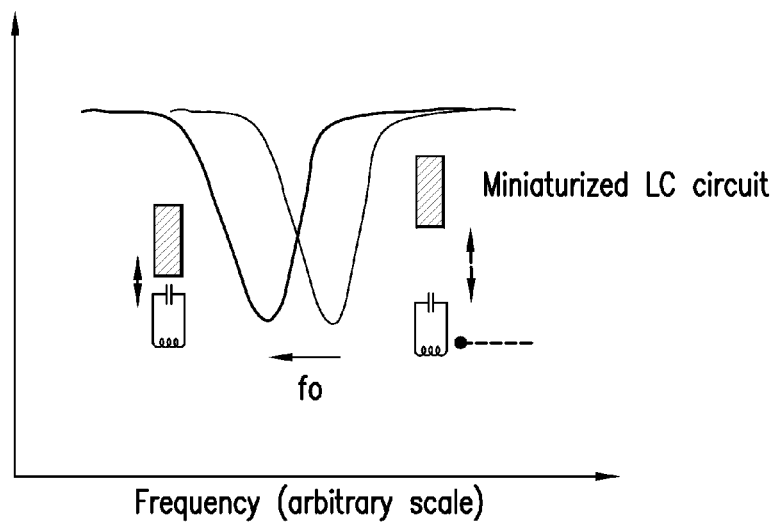

FIG. 9 schematically illustrates a typical screen-shot of a conventional network analyzer displaying the level of reflected power measured at the terminals of a single coil antenna connected to a S-parameter box.

Figure 10:
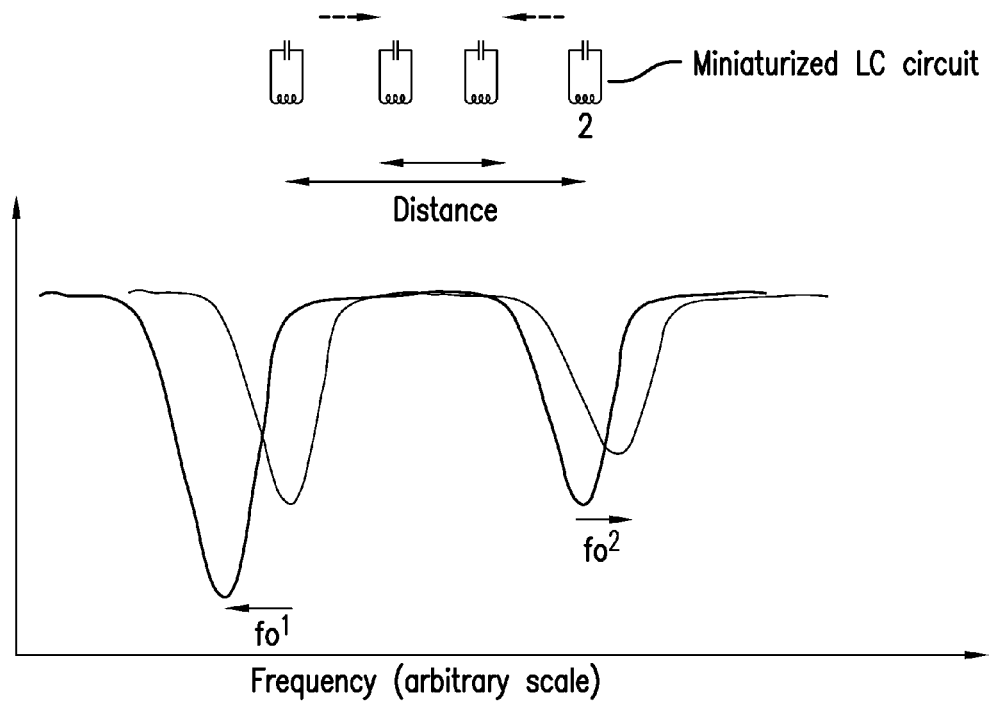

FIG. 10 schematically illustrates a typical screen-shot of a conventional network analyzer displaying the level of reflected power measured at the terminals of a single coil antenna connected to a S-parameter box.

Figure 11:
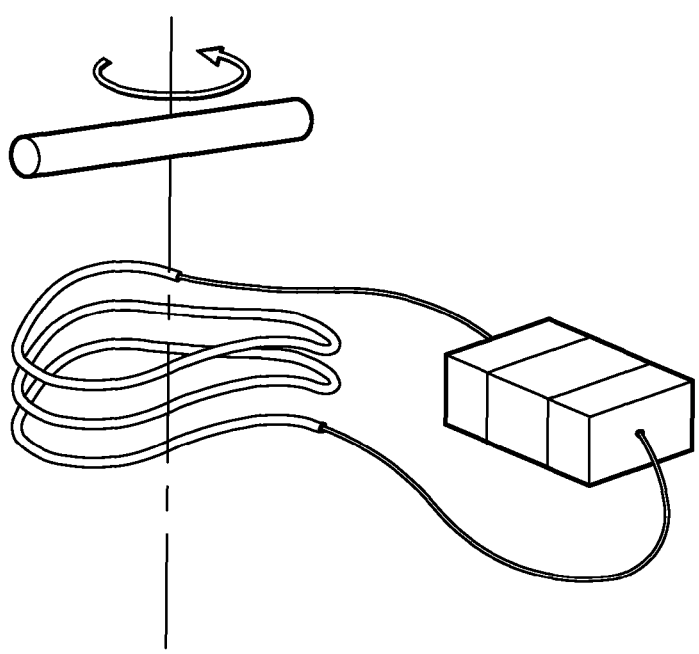

FIG. 11 schematically illustrates a coil inductor of the LC resonant circuit having a longitudinal axis, showing the respective windings of the coil inductor spiraling about and extending along the longitudinal axis, and further showing at least a portion of each winding of the coil is non-planer with respect to the longitudinal axis.

Figure 12:
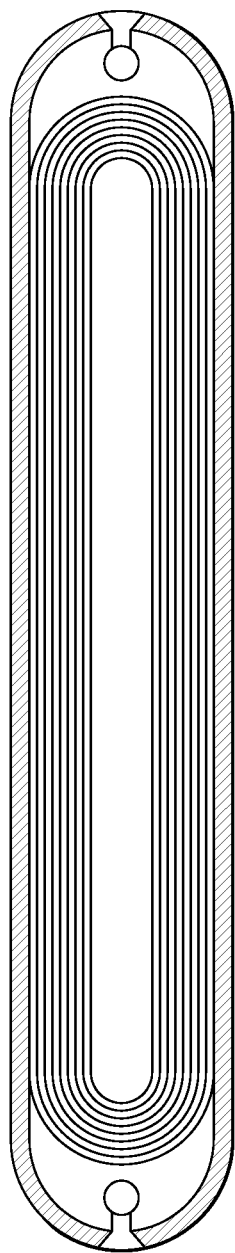

FIG. 12 schematically illustrates an exemplary substantially planar LC resonant circuit.

Figure 13:
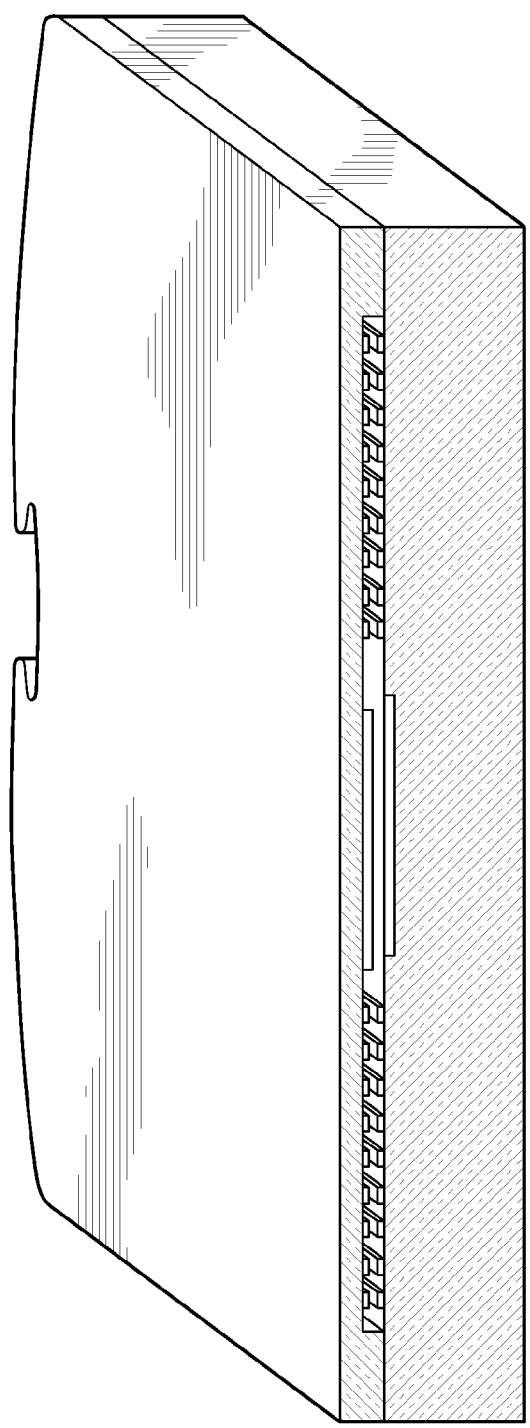

FIG. 13 is an exemplary cross-sectional perspective view of the LC resonant circuit of FIG. 12.

Figure 14:
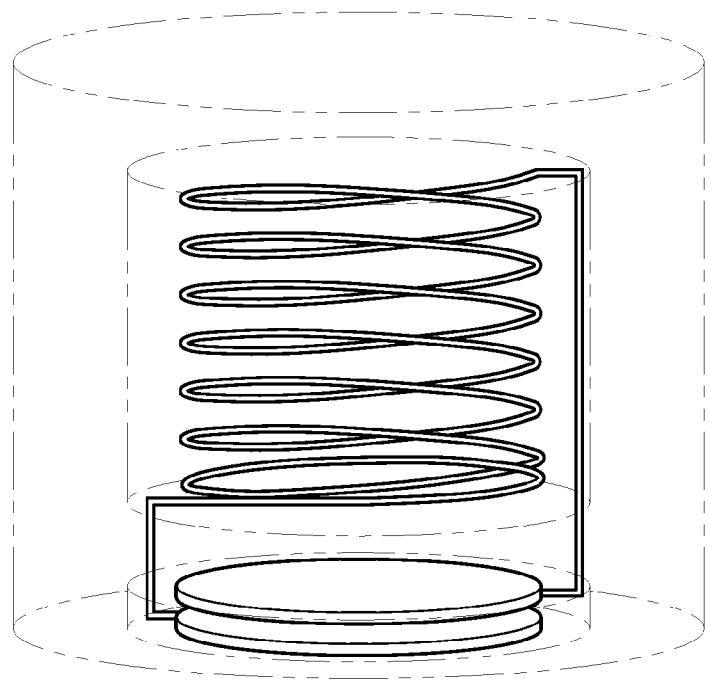
Figure 15:
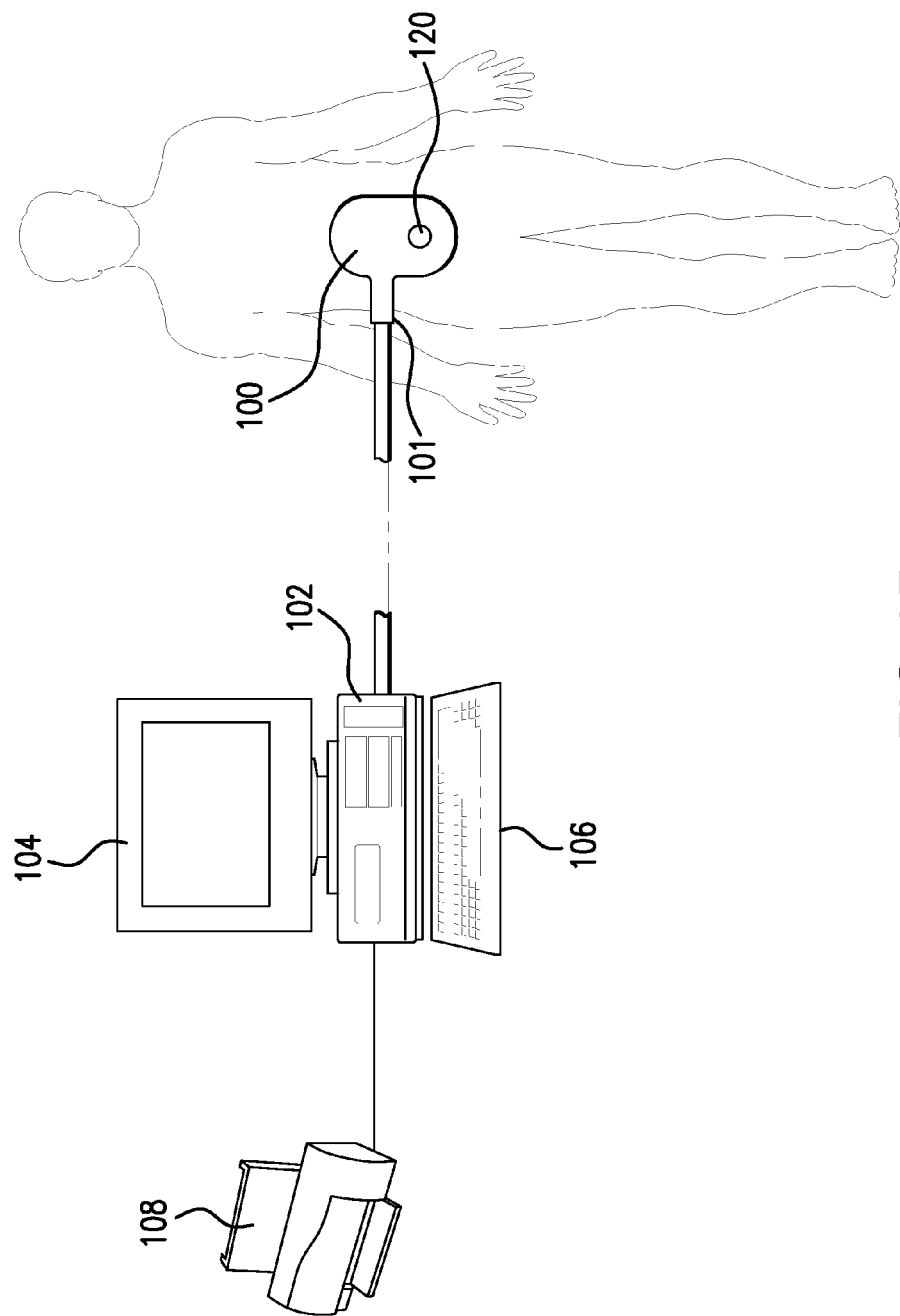

FIG. 14 schematically illustrates a coil inductor of an exemplary LC resonant circuit having a longitudinal axis, FIG. 15 illustrates an exemplary interrogation system for communicating with the first assembly that is positioned within a body.

Figure 16:
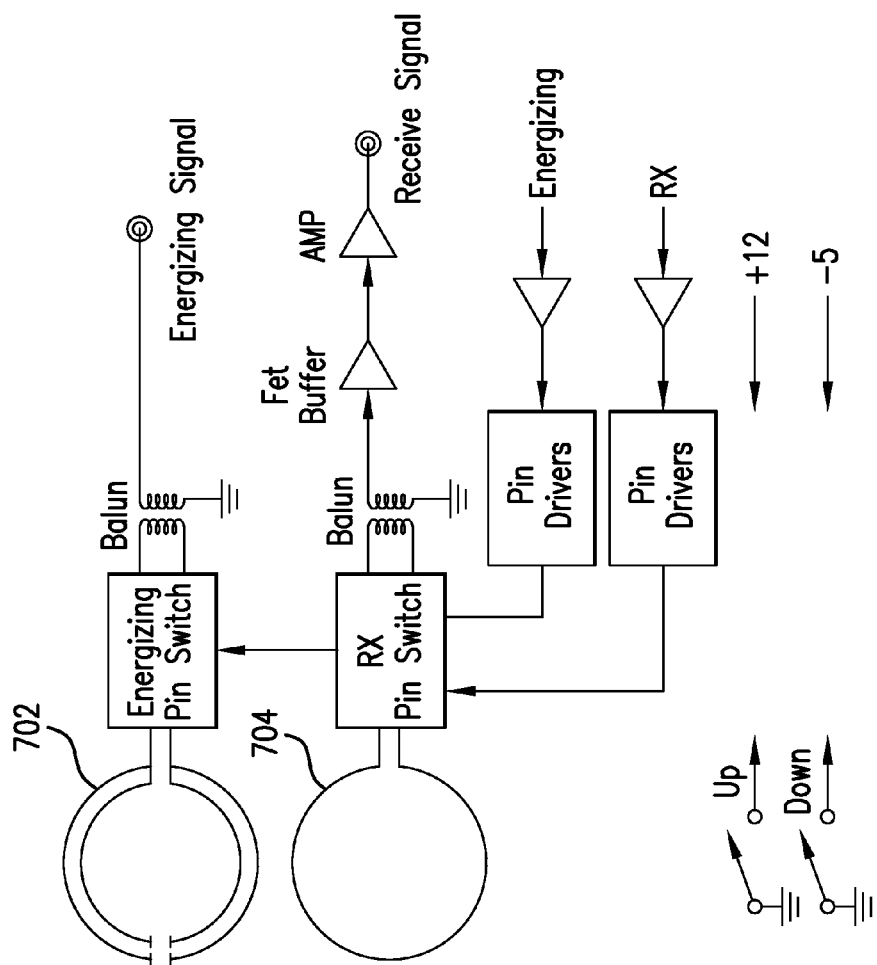

FIG. 16 is an exemplary block diagram of an exemplary coupling loop assembly for communication with a wireless sensor assembly.

FIG. 17A illustrates a exemplary coupling loop that is un-tuned and FIG. 17B illustrates its equivalent circuit.

FIG. 18A illustrates a loop that is tuned and FIG. 18B illustrates its equivalent circuit.

FIG. 19A illustrates a loop terminated into a receiver with a high input impedance and FIG. 19B illustrates its equivalent circuit.

FIG. 20 is a graph that illustrates the comparison of the frequency response for tuned loops and the frequency response for un-tuned loops with high input impedances at the receiver.

Figure 21:
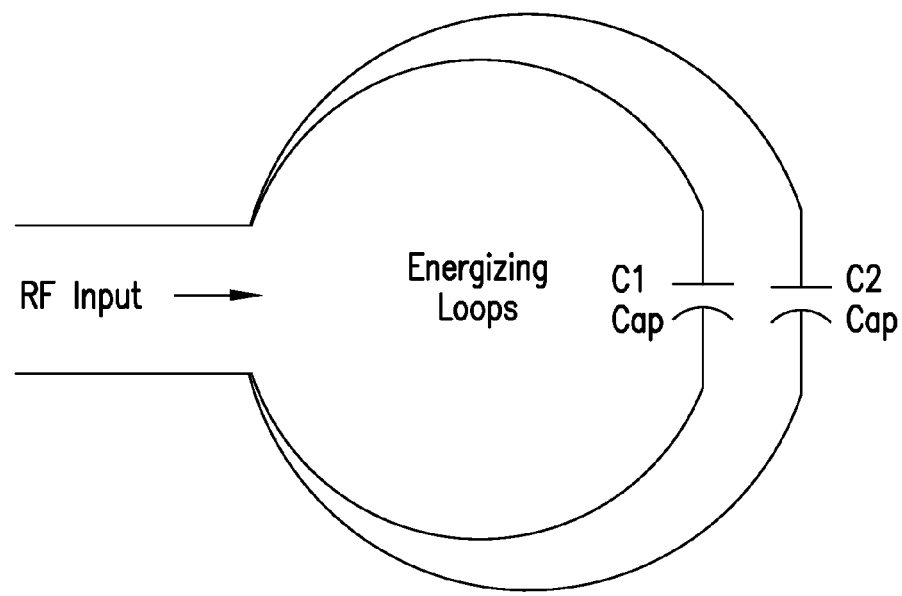

FIG. 21 schematically illustrated two stagger tuned loops.

Figure 22:
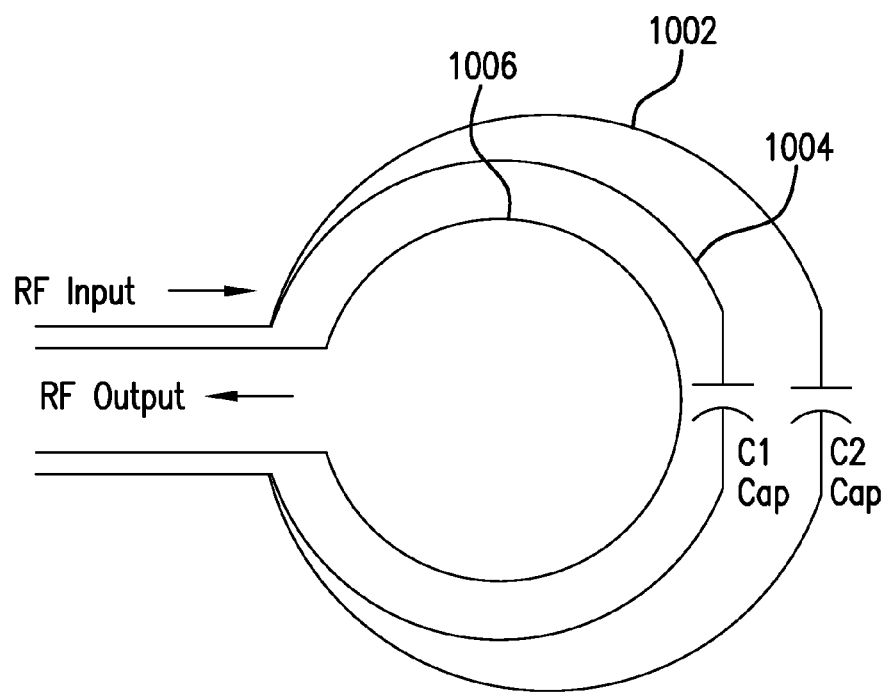

FIG. 22 illustrates the assembly of two stagger-tuned loops 1002, 1004 for transmitting the energizing signal to the passive electrical resonant circuit of the assembly and one un-tuned loop 1006 for receiving the output signal.

DETAILED DESCRIPTION OF THE INVENTION

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "an assembly" can include two or more such assemblies unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Commonly assigned U.S. patent application Ser. Nos. 12/175,803, 11/717,967, 11/613,645, 11/472,905, 11/276,571, 11/157,375, 11/105,294, and 10/943,772 are incorporated herein by reference in their entirety.

Embodiments provided herein comprise an apparatus and method of using same that can be configured to provide an in-vivo assessment of relative movement of an implant that is positioned in a living being. The implant can be any implant that is introduced into the living being and, in one non-limiting example, can comprise a prosthetic device for preserving motion between adjacent bones. In another non-limiting example, the implant can comprise an intervertebral cage.

Referring generally to FIGS. 1-8, in one aspect, the apparatus can comprise a first assembly 10 and a second assembly 20 that are selectively positioned within the living being in a spaced relationship. In one aspect, the first assembly 10 can comprise a passive electrical resonant circuit 12 that can be configured to be selectively interrogated with RF energy produced by a remote interrogator. The transmitted RF energy can be selected in order to selectively electromagnetically couple the passive electrical resonant circuit. As one will appreciate and as described in more detail below, the remote interrogator acts as an ex-vivo source of desired RF energy. In response to the electromagnetic coupling, the first assembly 10 can be is configured to generate an output signal characterized by a frequency that is dependent upon a distance between the first assembly 10 and the second assembly 20. In one aspect, at a first distance between the first assembly and the second assembly, the first assembly is configured, in response to the electromagnetic coupling, to generate a first output signal having a first frequency, and wherein, at a second distance between the first assembly and the second assembly that differs from the first distance, the first assembly will generate an output signal having a second frequency in response to the electromagnetic coupling that differs from the first frequency. The change to the frequency, which can for example be a change in the resonant frequency of the first assembly, allows for to the determination of the relative distance between the respective first and second assemblies.

Optionally, in various aspects, the second assembly 20 can comprise, for example and without limitation, a metallic element 22, a non-metallic element 24, and/or a passive electrical circuit 26. In one aspect, the non-metallic element can comprise magnetic properties. In one aspect, the passive electrical circuit 26 of the second assembly can comprise a passive electrical resonant circuit. Optionally, in a further aspect, the passive electrical resonant circuit of the second assembly 20 can be substantially identical to the passive electrical resonant circuit of the first assembly 10.

In one aspect, the passive electrical resonant circuit of the first assembly can be an electro-mechanical transducer that is capable of transforming a signal from one form of energy into another, namely from mechanical into electrical energy. In one aspect, it is contemplated that the passive electrical resonant circuit 12 of the first assembly 10 can comprise an inductance-capacitance ("LC") resonant circuit. Optionally, if used, the passive electrical resonant circuit 26 of the second assembly 20 can also comprise a LC resonant circuit. In this aspect, it is contemplated that the resonate frequency of the LC resonant circuit of the second assembly 20 would differ from a resonate frequency of the LC resonant circuit of the first assembly 10. In another aspect, the passive electrical resonant circuit 12 of the first assembly 10, and optionally the second assembly 20, can comprise a self-resonant inductor circuit.

Conventionally, a passive (no battery) LC resonant circuit is composed of two electrical passive components that are connected in series: (a) a coil, or inductor ("L"), (b) a capacitor ("C"). Such a passive electrical circuit exhibits electrical resonance when subjected to an alternating electromagnetic field. The electrical resonance is particularly acute for a specific frequency value or range of the impinging signal. When the impinging signal substantially reaches the resonant frequency of the LC resonant circuit inside the sensor assembly, a pronounced disturbance of the field can be detected wirelessly. In the simplest approximation, the electrical resonance occurs for a frequency f, related to the value of L and C according to equation 1:

$$f=(2\pi(LC)^{1/2})^{-1} \quad \text{(equation 1)}$$

The passive electrical resonant circuit for the assemblies described herein that utilize a passive electrical resonant circuit can be fabricated, for example and without limitation, via Micro Electro-Mechanical Systems ("MEMS") approach to sensor design, which lends itself to the fabrication of small sensors that can be formed using biocompatible polymers as substrate materials. In a further aspect, appropriately biocompatible coatings can be applied to the surfaces of the respective assemblies in order to prevent adhesion of biological substances to the respective assemblies that could interfere with their proper function. In one example, the passive electrical resonant circuit of the assembly can be manufactured using Micro-machining techniques that were developed for the integrated circuit industry. An example of this type of sensor features an inductive-capacitive resonant circuit with a variable capacitor is described in Allen et al., U.S. Pat. No. 6,111,520, which is incorporated herein by reference. In this sensor, the capacitance varies with the pressure of the environment in which the capacitor is placed. Consequently, the resonant frequency of the exemplary LC circuit of the Allen pressure sensor varies depending on the pressure of the environment.

The proximity of magnetic materials, such as, for example and without limitation, ferrite or permanent magnet, can be detected wirelessly by monitoring the resonant frequency of the exemplary wireless LC resonant circuit. When the magnetic material of the second assembly remains far enough away from the LC resonant circuit of the first assembly, the resonant frequency of the first assembly circuit can be calculated using equation 1 above. As the LC resonant circuit of the first assembly is brought into proximity of the magnetic material of the second assembly, the resonant frequency of the LC resonant circuit of the first assembly changes as a direct result of the change in the inductance value of the LC resonant circuit. In one aspect, magnetic materials with high relative permeability at the frequency of interest can have a particularly strong effect on the value of the inductance of the LC resonant circuit.

FIG. 9 schematically illustrates a typical screen-shot of a conventional network analyzer displaying the level of reflected power measured at the terminals of a single coil antenna connected to a S-parameter box. The dip in the curve indicates the resonance of the LC resonant circuit of the first assembly, in the frequency domain, in absence of magnetic materials. The dip was experimentally observed to shift to the left, i.e., decrease, as the second assembly, here an exemplary piece of magnetic material, e.g., ferrite, was brought in close proximity to the LC resonant circuit of the first assembly. The embodiments of the system described herein below comprising the apparatus described above and a wireless interrogation system can to monitor the resulting change in frequency. After calibration, the noted shift in frequency can be analyzed to determine the proportional change in distance between the LC resonant circuit of the first assembly and the magnetic material of the second assembly.

Similarly, a frequency shift can be observed when an LC resonant circuit of the first assembly 10 is brought into close proximity to an LC resonant circuit of the second assembly 20. In this example, the respective LC resonant circuits of the first and second assemblies have fundamental resonant frequencies $fo_1$ and $fo_2$ that are predictably calculated using equation 1. However, as the respective LC resonant circuits are brought into proximity to each other, the resonant frequency of both of the assemblies changes as a result of a change in the mutual inductance. It is also contemplated that the Q factor can also change as the respective LC resonant circuits are brought into proximity to each other.

FIG. 10 schematically illustrates a typical screen-shot of a conventional network analyzer displaying the level of reflected power measured at the terminals of a single coil antenna connected to a S-parameter box. The two respective dips in the curve indicate the fundamental resonance of the LC resonant circuits of the respective first and second assemblies, in the frequency domain. The respective dip of the LC resonant circuit of the first assembly was experimentally observed to shift to the left, i.e., decrease, and the respective dip of the LC resonant circuit of the second assembly was experimentally observed to shift to the right, i.e., increase, as the LC resonant circuit of the second assembly was brought in close proximity to the LC resonant circuit of the first assembly. The embodiments of the system described herein below comprising the apparatus described above and a wireless interrogation system is able to monitor the resulting change in frequency. After calibration, the noted shift in frequency of the first assembly can be analyzed to determine the proportional change in distance between the LC resonant circuit of the first assembly and the LC resonant circuit of the second assembly. Of course, in this embodiment, it is also contemplated that the shift in frequency of the second assembly can be analyzed to determine the proportional change in distance between the LC resonant circuit of the first assembly and the LC resonant circuit of the second assembly.

As described above, it is contemplated that the LC resonant circuit can comprise a coil inductor operably coupled to a capacitor. In various aspects, the inductance of the LC resonant circuit can be between about 0.1 to about 1000 micro-Henry, preferably between about 1 to about 100 micro-Henry, and more preferably between about 5 to about 15 micro-Henry. The capacitance of the LC resonant circuit can be between about 0.1 to about 1000 pF, preferably between about 0.5 to about 100 pF, and more preferably between about 1 to about 20 pF. The resonant frequency of the LC resonant circuit can be between about 0.1 to about 450 MHz, preferably between about 1 to about 60 MHz, and more preferably between about 25 to about 45 MHz. In addition, the quality factor at self resonance and the frequency range of the self-resonant frequency itself can be between about 5 to 120, preferably between about 5 to about 80, and more preferably between about 10 to about 70.

There are various manufacturing techniques that can be employed to realize sensors assemblies according to the current invention. Capacitors and inductors made by a variety of methods can be manufactured separately, joined through interconnect methods and encapsulated in non-permeable packaging. In one embodiment, the pressure sensitive capacitor and the three-dimensional inductor coil are formed separately and joined together to form the LC circuit. In another embodiment, the capacitor and inductor coil can be manufactured integral with one another. Additionally, there are several methods to create these discrete elements and to join each discrete element to create the final sensor assembly.

Q factor (Q) is the ratio of energy stored versus energy dissipated. The reason Q is important is that the ring down rate of the sensor assembly is directly related to the Q. If the Q is too small, the ring down rate occurs over a substantially shorter time interval. This necessitates faster sampling intervals, making sensor detection more difficult. Also, as the Q of the sensor increases, so does the amount of energy returned to external electronics. Thus, in one aspect, the sensor assembly can be configured with values of Q sufficiently high enough to avoid unnecessary increases in complexity in communicating with the sensor assembly via external electronics.

The Q of the sensor assembly can be dependent on multiple factors such as, for example and without limitation, the shape, size, diameter, number of turns, spacing between the turns and cross-sectional area of the inductor component. In addition Q will be affected by the materials used to construct the sensor assembly. In one example, the sensor assembly can be formed from materials with low loss tangents to effect a sensor assembly with higher Q factors.

In one aspect, the coil inductor of the LC resonant circuit can be a substantially planar spiral inductor. Optionally, the coil inductor of the LC resonant circuit can have a longitudinal axis and the respective windings of the coil inductor can spiral about and extend along the longitudinal axis. In this aspect and referring to FIG. 11, at least a portion of each winding of the coil is non-planer with respect to the longitudinal axis. For example, in a representative cross-sectional plane that is substantially transverse to the longitudinal axis, portions of the windings in the y-axis can be below the cross-sectional plane and portions of the winding in the y-axis can be above the cross-sectional plane.

In one aspect, the inductor coil can be comprised of the inductor coil body and the coil leads. One skilled in the art will appreciate that numerous parameters of the inductor coil can be varied to optimize the balance of size and the electrical properties of the circuit, including the materials, coil diameter, wire gage, number of coil windings, and cross-sectional area of the coil body. Typically, the material of the coil must be highly conductive and also biocompatible. Suitable materials include, but are not limited to, gold, copper and alloys thereof. If the wire is sufficiently strong, the coil can be self-supporting, also known as an "air core" configuration. A solenoid coil is another suitable configuration. If the wire is not sufficiently strong to be unsupported to maintain its intended configuration during assembly and in use, the coil can be formed around a central bobbin comprised of a suitable dielectric material. In the alternative, the wound coil can be encased in a liquid polymer that can cure or otherwise harden after it is applied to the coil body. Polyimide is one preferred material for this application because of its thermal, electrical, and mechanical properties. However, processes achieving substantially similar results that involve lower processing temperatures would make other polymer choices desirable, such choices being obvious to one skilled in the art.

Optionally, it is contemplated that the passive electrical circuit of the sensor assembly can be housed within a substantially non-permeable enclosure to ensure the protection of the passive electrical circuit of the sensor assembly when the respective sensor assembly is positioned within the living being. In this aspect, the passive electrical circuit of the sensor assembly can be protected from deleterious agents such as corrosion, parasitic excessive strain/stress, biological response, etc. . . . As one will appreciate, it is contemplated that the enclosure can be formed of materials that substantially prevent any undesired fluids and/or gases from passing or diffusing through the walls of the enclosure, utilizing manufacturing processes that eliminate undesired holes that could otherwise permit such passing of undesired fluids or gases. In another aspect, the enclosure can be formed of materials that do not allow any undesired fluids and/or gases from passing or diffusing through the walls of the enclosure. Exemplary enclosure material can include, without limitation, biocompatible polymer (such as, for example and without limitation, PEAK, PE, PTFE, FEP, semi-crystalline thermoplastic polymers, and the like), glass, fused-silica, low temperature glass, ceramics, quartz, pyrex, sapphire, sintered zirconia and the like. An acceptable level of permeability can be a rate of fluid ingress or egress that changes the original capacitance of the LC circuit by an amount preferably less than 10 percent, more preferably less than 5 percent, and most preferably less than 1 percent over the accumulated time over which measurements will be taken.

Optionally, it is also contemplated that the housing can define an internal cavity in which at least a portion of the passive electrical circuitry can be disposed. In a further aspect, a known and invariant quantity of gas can be added to the internal cavity of the housing. In another aspect, it is contemplated that the enclosure can be formed of materials that will not allow the resonant circuit of the assembly to flex in response to relative motion of the implant that the sensor assembly is mounted thereon or other forces that can be otherwise applied to the exterior surface of the assembly.

In another aspect, the exemplary enclosure materials help to provide the desired biocompatibility, non-permeability and/or manufacturing processing capabilities of the assembly containing the resonant circuit. These exemplary materials are considered dielectrics, that is, they are poor conductors of electricity but are efficient supporters of electrostatic or electroquasistatic fields. A dielectric material has the ability to support such fields while dissipating minimal energy. In this aspect, the lower the dielectric loss, the lower the proportion of energy lost, and the more effective the dielectric material is in maintaining high Q.

With regard to operation within the human body, there is a second important issue related to Q, namely that blood and body fluids are conductive mediums and are thus particularly lossy. As a consequence, when an assembly having a resonant circuit is immersed in a conductive fluid, energy from the sensor assembly will dissipate, substantially lowering the Q and reducing the assembly-to-electronics distance. In one aspect, the loss can be minimized by further separation of the assembly having the resonant circuit from the conductive liquid, which can be accomplished, for example and without limitation, by coating at least a portion of the assembly having the resonant circuit in a suitable low-loss-tangent dielectric material.

In various aspects, it is contemplated that at least one of the first assembly or the second assembly can be operably coupled to a portion of the implant. It is also contemplated that at least one of the first assembly or the second assembly can be operably coupled to bone tissue proximate the implant. Optionally, both of the respective first and second assemblies can be operably coupled to spaced portions of the implant. In another aspect, it is contemplated that both of the respective first and second assemblies can be operably coupled to adjacent bone tissue.

Further, one skilled in the art will appreciate that it is contemplated that a portion of the implant itself can form the second assembly. In this aspect, the portion of the implant that forms the second assembly can be formed of magnetic materials, such as, for example and not meant to be limiting, a magnetized metallic material.

It is further contemplated that the first assembly can comprise a plurality of first assemblies and the second assembly can comprise a plurality of second assemblies. As one will appreciate, by using a plurality of opposed first and second assemblies, the respective distances between respective pairs of the opposed first and second assemblies can be determined and the relative position of implant can be derived from the determined distances when compared to the known shape of the implant and the known original implanted distances between the respective pairs of the opposed first and second assemblies.

It is contemplated in various aspects that the respective first and second assemblies can be positioned as described above and as exemplified in the figures to sense, in non-limiting examples, movement of at least a portion of the implant relative to at least another portion of the implant, movement of at least a portion of the implant relative to at least a portion of the tissue of the patient, such as, for example and without limitation, adjacent bone tissue, and the like.

In another example, it is contemplated to fixate a first assembly at the base of a bore hole in a bone tissue of the patient. The first assembly can exemplarily be fixed using a conventional bone cement. Subsequently, a fastener, such as, for example and without limitation, a pedicle screw, can be mounted therein the bore hole such that it is positioned at a distance from the mounted first assembly. In this example, the second assembly can be mounted to or can be integral with the fastener. In one aspect, the fastener itself can serve as the second assembly. It will be appreciated that the apparatus and system described herein can be used in this aspect to monitor the relative position of the fastener to the first assembly. In operation, a shift in the sensed resonance frequency of the first assembly, i.e., a sensed increase in the resonance frequency of the first assembly, can be an indication of movement of the fastener outwardly away from the first assembly. Optionally, it is of course contemplated that a second assembly can be mounted therein the bore hole and the first assembly can be mounted to or formed integrally within the fastener.

As described above, in one embodiment, an assembly having a resonant circuit can comprise a passive LC resonant circuit with a varying capacitor. Because the exemplary assembly can be fabricated using passive electrical components and has no active circuitry, it does not require on-board power sources such as batteries, nor does it require leads to connect to external circuitry or power sources. These features create a assembly which is self-contained within the enclosure and lacks physical interconnections that traverse the hermetic enclosure or housing.

Because of the presence of the inductor in the LC resonant circuits described herein, it is possible to couple to the assembly having the LC resonant circuit electromagnetically and to induce a current in the LC resonant circuit via a magnetic loop. This characteristic allows for wireless exchange of electromagnetic energy with the assembly and the ability to operate it without the need for an on-board energy source such as a battery. Thus, using the system described herein, it is possible to determine the relative movement between the respective first and second assemblies by a simple, non-invasive procedure by remotely interrogating the assembly or assemblies, detecting and recording the resonant frequency, and converting this value to a strain or stress measurement.

In a further aspect, the system for providing an in-vivo assessment of relative movement of an implant in a living being of embodiments described herein can comprise an ex-vivo source of RF energy and the respective first and second assemblies described above. In one aspect, the first assembly can comprise passive electrical resonant circuit positioned within the living being that is configured to be selectively electromagnetically coupled to the ex-vivo source of RF energy. The first assembly can be configured to generate an output signal characterized by a frequency that is dependent upon a distance between the first assembly and the second assembly in response to the electromagnetic coupling.

In a further aspect, the system can comprises a means for monitoring the output signal of the first assembly, which frequency can comprises the resonant frequency of the first assembly. In one exemplary aspect, the means for monitoring the output signal of the first assembly can comprise a means for detecting or otherwise receiving the output signal of the first assembly and a processor, or similar processing means, configured to determine the relative distance between the respective first and second assemblies based on the frequency of the output signal produced by the first assembly. It is of course contemplated that, if the second assembly is an LC resonant circuit, the system can optionally comprise a means for monitoring the resonant frequency of the output signal from the second assembly to determine the relative distance between the respective first and second assemblies based on the frequency of the output signal of the second assembly.

In another aspect, the system described herein provides for a system capable of determining the resonant frequency and bandwidth of the first assembly using an impedance approach. In this approach, an excitation signal can be transmitted using a transmitting antenna to electromagnetically couple an assembly having a passive electrical resonant circuit to the transmitting antenna, which resultingly modifies the impedance of the transmitting antenna. The measured change in impedance of the transmitting antenna allows for the determination of the resonant frequency and bandwidth of the passive electrical resonant circuit of the assembly.

In a further aspect, the system described herein provides for a transmit and receive system configured to determine the resonant frequency and bandwidth of a resonant circuit within a particular assembly. In this exemplary process, an excitation signal of white noise or predetermined multiple frequencies can be transmitted from a transmitting antenna and the passive electrical resonant circuit of the assembly is electromagnetically coupled to the transmitting antenna. A current is induced in the passive electrical resonant circuit of the assembly as it absorbs energy from the transmitted excitation signal, which results in the oscillation of the passive electrical circuit at its resonant frequency. A receiving antenna, which can also be electromagnetically coupled to the transmitting antenna, receives the excitation signal minus the energy which was absorbed by the assembly. Thus, the power of the received or output signal experiences a dip or notch at the resonant frequency of the assembly. The resonant frequency and bandwidth can be determined from this notch in the power. In one aspect, the transmit and receive methodology of determining the resonant frequency and bandwidth of a passive electrical resonant circuit of an assembly can include transmitting a multiple frequency signal from a transmitting antenna to electromagnetically couple the passive electrical resonant circuit on the sensor assembly to the transmitting antenna in order to induce a current in the passive electrical resonant circuit of the assembly. A modified transmitted signal due to the induction of current in the passive electrical circuit is received and processed to determine the resonant frequency and bandwidth.

In another aspect, the system can determine the resonant frequency and bandwidth of a passive electrical resonant circuit within a particular assembly by using a chirp interrogation system, which provides for a transmitting antenna that is electromagnetically coupled to the resonant circuit of the assembly. In this aspect, an excitation signal of white noise or predetermined multiple frequencies can be applied to the transmitting antenna for a predetermined period of time to induce a current in the passive electrical resonant circuit of the assembly at the resonant frequency. The system then listens or otherwise receives an output signal that radiates from the energized passive electrical resonant circuit of the assembly. In this aspect, the resonant frequency and bandwidth of the passive electrical resonant circuit can be determined from the output signal. In this aspect, the chirp interrogation method can include transmitting a multi-frequency signal pulse from a transmitting antenna; electromagnetically coupling a passive electrical resonant circuit on an assembly to the transmitting antenna to induce a current in the resonant circuit; listening for and receiving an output signal radiated from the energized passive electrical signal of the assembly; determining the resonant frequency and bandwidth from the output signal, and resultingly, determining the distance between the respective first and second assemblies from the determined resonant frequency and bandwidth.

In a further aspect, the system described herein can provide an analog system and method for determining the resonant frequency of a passive electrical resonant circuit within a particular assembly. The analog system can comprise a transmitting antenna coupled as part of a tank circuit, which, in turn, is coupled to an oscillator. In this aspect, a signal is generated which oscillates at a frequency determined by the electrical characteristics of the tank circuit. The frequency of this signal is further modified by the electromagnetic coupling of the passive electrical resonant circuit of the assembly. This signal can be applied to a frequency discriminator that provides a signal from which the resonant frequency of the resonant circuit can be determined. In this aspect, the analog method can include generating a transmission signal using a tank circuit that includes a transmitting antenna; modifying the frequency of the transmission signal by electromagnetically coupling the passive electrical resonant circuit of the assembly to the transmitting antenna; and converting the modified transmission signal into a standard signal for further application.

One exemplary method of interrogation is explained in more detail in commonly assigned U.S. patent application Ser. No. 11/105,294. In the described methodology, the interrogating system energizes the assembly having the resonant circuit with a low duty cycle, gated burst of RF energy having a predetermined frequency or set of frequencies and a predetermined amplitude. The energizing signal is coupled to the passive electrical resonant circuit via a magnetic loop. The energizing signal induces a current in the passive electrical resonant circuit that is maximized when the frequency of the energizing signal is substantially the same as the resonant frequency of the passive electrical resonant circuit. The system receives the ring down response of the assembly via magnetic coupling and determines the resonant frequency of the assembly, which is then used to determine the relative distance between the respective first and second assemblies. In one aspect, the resonant frequency of the assembly is determined by adjusting the frequency of the energizing signal until the phase of the ring down signal and the phase of a reference signal are equal or at a constant offset. In this manner, the energizing signal frequency is locked to the assembly's resonant frequency and the resonant frequency of the assembly is known. The relative distance can then be ascertained.

In one aspect, the system can comprise a coupling loop that can be selectively positioned relative to the first and second sensor assemblies to maximize the electromagnetic coupling between the passive electrical resonant circuit of the assembly and the coupling loop. The system can also provide the necessary isolation between the energizing signal and the output signal. In one aspect, it is contemplated that the system can energize the passive electrical resonant circuit of the assembly with a low duty cycle, gated burst of RF energy having a predetermined frequency or set of frequencies and a predetermined amplitude. The energizing signal can be electromagnetically coupled to the passive electrical resonant circuit of the assembly via one or more energizing loops. In operation, each energizing loop can be tuned to a different resonant frequency. The selection of the desired resonant frequencies can be based on the desired bandwidth, which, in one aspect of the invention and without limitation can range between about 30 to about 37.5 MHz.

The energizing signal induces a current in the passive electrical resonant circuit of the assembly that is maximized when the energizing frequency is the same as the resonant frequency of the passive electrical resonant circuit of the assembly. The system receives the ring down response of the assembly (or assemblies) via one or more coupling loops and determines the resonant frequency of the sensor, which can be used to calculate the distance between the respective first and second assemblies.

In one aspect, a pair of phase locked loops ("PLLs") can be used to adjust the phase and the frequency of the energizing signal until its frequency locks to the resonant frequency of the passive electrical resonant circuit of the assembly. In one embodiment, one PLL samples during the calibration cycle and the other PLL samples during the measurement cycle. In one non-limiting example, these cycles can alternate every 10 microseconds and can be synchronized with the pulse repetition period. In one aspect, the calibration cycle adjusts the phase of the energizing signal to a fixed reference phase to compensate for any system delay or varying environmental conditions. The environmental conditions that can affect the accuracy of the reading can include, but are not limited to, proximity of reflecting or magnetically absorbative objects, variation of reflecting objects located within transmission distance, variation of temperature or humidity which can change parameters of internal components, and aging of internal components.

In one aspect, one of the PLLs can be used to adjust the phase of the energizing signal and is referred to herein as the fast PLL. The other PLL can be used to adjust the frequency of the energizing signal and is referred to herein as the slow PLL. During the time that the energizing signal is active, a portion of the signal enters the receiver and is referred to herein as a calibration signal. The calibration signal is processed and sampled to determine the phase difference between its phase and the phase of a local oscillator. The cycle in which the calibration signal is sampled is referred to as the calibration cycle. In one aspect, the system can adjust the phase of the energizing signal to drive the phase difference to zero or another select reference phase.

During the measurement cycle, the signal coupled from the passive electrical resonant circuit of the assembly (referred to herein as the output signal) can be processed and sampled to determine the phase difference between the output signal and the energizing signal. The system can then adjust the frequency of the energizing signal to drive the phase difference to zero or other reference phase. Once the slow PLL is locked, the frequency of the energizing signal is deemed to match the resonant frequency of the passive electrical resonant circuit of the assembly. The operation of the slow PLL is qualified based on signal strength so that the slow PLL does not lock unless the strength of the output signal meets a predetermined signal strength threshold.

In one aspect, a single un-tuned coupling loop can be is used. In this exemplary aspect, the loop can be connected to an input impedance that is high relative to the loop inductance. Optionally, multiple coupling loops can be used and each loop is tuned to a different resonant frequency.

In another aspect, the loops can be connected to a base unit that generates the energizing signal and processes the output signal via a cable assembly. In this aspect, the cable assembly provides isolation between the energizing signal and the sensor signal by maximizing the distance between the coaxial cables that carry the signals and maintaining the relative positions of the coaxial cables throughout the cable assembly. In another exemplary aspect, the coaxial cables can be positioned on opposite sides of an internal cable, approximately 180 degrees apart. Shielding can also be used to isolate the energizing signal from the output signal. In one aspect, it is contemplated that additional shielding can be provided around each of the respective coaxial cables.

In one aspect, FIG. 15 illustrates an exemplary interrogation system for communicating with the wireless apparatus described above that is positioned within a body. Without limitation, it is contemplated that the system can be used in at least two environments: the operating room during implant and the physician's office during follow-up examinations.

In one exemplary embodiment, the interrogation system can comprise a coupling loop 100, a base unit 102, a display device 104, and an input device 106, such as, for example and without limitation, a keyboard. In one exemplary embodiment, the base unit can include an RF amplifier, a receiver, and signal processing circuitry. In one aspect, the coupling loop 100 can be configured to charge the passive electrical resonant circuit of the assembly and then couple signals from the energized passive electrical resonant circuit of the assembly into the receiver. Schematic details of the exemplary circuitry are illustrated in FIG. 15.

The display 104 and the input device 106 can be used in connection with the user interface for the system. In the embodiment illustrated in FIG. 15, the display device and the input device are conventionally connected to the base unit. In this embodiment, the base unit can also provides conventional computing functions. In other embodiments, the base unit can be connected to a conventional computer, such as a laptop, via a communications link, such as an RS-232 link. If a separate computer is used, then the display device and the input devices associated with the computer can be used to provide the user interface. In one embodiment, LABVIEW software can be used to provide the user interface, as well as to provide graphics, store and organize data and perform calculations for calibration and normalization. The user interface can record and display patient data and guide a user through surgical and follow-up procedures. In another aspect, an optional printer 108 can be operably connected to the base unit and can be used to print out patient data or other types of information. As will be apparent to those skilled in the art in light of this disclosure, other configurations of the system, as well as additional or fewer components can be utilized with embodiments of the invention.

In one embodiment, the coupling loop can be formed from a band of copper. In this aspect, it is contemplated that the coupling loop comprises switching and filtering circuitry that is enclosed within a shielded box. The loop can be configured to charge the passive electrical resonant circuit of the assembly and then couple signals from the energized passive electrical resonant circuit of the assembly sensor into a receiver. It is contemplated that the antenna can be shielded to attenuate in-band noise and electromagnetic emissions.

In an alternative embodiment for a coupling loop, as shown in FIG. 16, separate loops for energizing 702 and for receiving 704 are provided, although a single loop can be used for both functions. PIN diode switching inside the loop assembly can be used to provide isolation between the energizing phase and the receive phase by opening the RX path pin diodes during the energizing period, and opening the energizing path pin diodes during the coupling period. It is contemplated in this embodiment that multiple energizing loops can be staggered tuned to achieve a wider bandwidth of matching between the transmit coils and the transmit circuitry.

In one aspect, the coupling loop or antenna can provide isolation between the energizing signal and the output signal, support sampling/reception of the output signal soon after the end of the energizing signal, and minimize switching transients that can result from switching between the energizing and the coupled mode. The coupling loop can also provide a relatively wide bandwidth, for example from between about X to about Y and preferable from between about 30 to about 37.5 MHz.

In one embodiment, separate loops can be used for transmitting the energizing signal to the passive electrical resonant circuit of the assembly and coupling the output signal from the energized passive electrical resonant circuit of the assembly. Two stagger-tuned loops can be used to transmit the energizing signal and an un-tuned loop with a high input impedance at the receiver can be used to receive the output signal. The term "coupling loop" is used herein to refer to both the loop(s) used to receive the output signal from the energized passive electrical resonant circuit of the assembly (the "assembly coupling loop"), as well as the loop assembly that includes the loop(s) used to transmit the energizing signal to the passive electrical resonant circuit of the assembly (the "energizing loop") and the assembly coupling loop(s).

During the measurement cycle, the assembly coupling loop can be configured to couple the output signal from the energized passive electrical resonant circuit of the assembly, which is relatively weak and dissipates quickly. In one aspect, the voltage provided to the receiver in the base unit depends upon the design of the assembly coupling loop and in particular, the resonant frequency of the loop.

In a further aspect, it is contemplated that the coupling loop can be un-tuned or tuned. FIG. 17A illustrates a loop that is un-tuned and FIG. 17B illustrates its equivalent circuit. The loop has an inductance, $L_1$, and is terminated into the receiver using a common input impedance, which can, for example and without limitation, be 50 ohms. The voltage at the receiver, $V_1$, is less than the open circuit voltage of the loop, i.e., the voltage that would be coupled by the loop if the loop was not terminated, $V_s$, and can be calculated as shown below.

$$V_1 = V_s \frac{50}{50 + j\omega L_1} \quad \text{Equation 2}$$

Where L1 is the inductance of the loop and $\omega = 2\pi f$, with f=frequency in hertz.

To maximize the voltage at the receiver, it is contemplated that the loop can be tuned. FIG. 18A illustrates a loop that is tuned and FIG. 18B illustrates its equivalent circuit. In this aspect, the loop has an inductance, $L_1$, and a capacitance, $C_1$. The capacitance, $C_1$, is selected so that it cancels the inductance, $L_1$ at the resonant frequency, i.e., the series resonant circuit, $C_1$-$L_1$, is 0 ohms at the resonant frequency. At the resonant frequency the voltage at the receiver, $V_1$, equals the voltage coupled by the loop, $V_s$. One disadvantage of this type of loop is that it is optimized for a single frequency. If the loop is used in an environment where the frequency of the output signal is changing, then the capacitance is either changed dynamically or set to a compromise value (e.g., the loop is tuned to a single frequency within the band of interest).

To minimize this issue, another embodiment illustrated in FIGS. 19A and 19B uses an un-tuned loop with a high input impedance at the receiver. FIG. 19A illustrates a loop terminated into a receiver with a high input impedance and FIG. 19B illustrates its equivalent circuit. In this aspect, the input impedance at the receiver is selected so that the energy lost due to the loop impedance, $L_1$, is relatively insignificant. Using Zin as the input impedance at the receiver, the voltage at the receiver, $V_1$, is calculated as shown below.

$$V_1 = V_s \frac{Zin}{Zin + j\omega L_1} \quad \text{Equation 3}$$

Since Zin is much larger than $j\omega L_1$, this can be approximated by the following equation $$V_1 = V_s \frac{\infty}{\infty + j\omega L_1}, \text{ or } V_1 = V_s \quad \text{Equation 4}$$

As shown by the foregoing equation, the use of a relatively high input impedance at the input of the receiver negates $L_1$ for all frequencies. In one embodiment, a high impedance buffer can be inserted between the loop and an exemplary 50 ohm receiver circuit. In this embodiment, the high impedance buffer is on the order of 1 Mohm while the impedance of the loop is on the order of 200 ohms. In other embodiments, it is contemplated that the input impedance is at least two times the loop impedance.

In one aspect, the frequency response within the band of interest is more monotonic if the assembly coupling loop uses a high input impedance at the receiver, than if a tuned loop is used with a 50 ohm input impedance. FIG. 20 compares the frequency response for tuned loops and the frequency response for un-tuned loops with high input impedances at the receiver. The y-axis represents the difference in measured frequency between a calibration system using a network analyzer and the loop. The x-axis represents the frequency of the L-C standard used in the measurements. Linear interpolation was used between measurement points. Band 1 corresponds to a loop resonant at 32 MHz, Band 2 corresponds to a loop resonant at 35 MHz, Band 3 corresponds to a loop resonant at 38 MHz, and Band 4 corresponds to a loop resonant at 41 MHz. Bands 1-4 correspond to a prior art design that uses switched capacitors banks to vary the loop resonance to achieve the needed bandwidth. Bands 5 and 6 correspond to un-tuned loops.

Bands 1-4 illustrate a slope variation within the band of interest, which can affect the accuracy of measurements made using the loop. Bands 5 and 6 illustrate that the variation within the band of interest is less than in the systems using a tuned loop. The more monotonic frequency response of an un-tuned loop with a high input impedance requires a simpler set of calibration coefficients to be used for the frequency conversion calculation.

An alternative embodiment to using an un-tuned loop and a high input impedance is to use stagger-tuned loops. If stagger tuned loops are used to receive the output signal, then the loops can be tuned in a manner similar to that described in the following paragraphs in connection with the transmission of an energizing signal.

During the energizing mode, the energizing loop produces a magnetic field. The intensity of the magnetic field produced by the energizing loop depends, in part, on the magnitude of the current within the loop. In one aspect, the current is maximized at the energizing frequency if the impedance of the loop is essentially 0 ohms at the energizing frequency. The resonant frequency of the loop is related to the loop inductance and capacitance, as shown below.

$$f_o = \frac{1}{2\pi\sqrt{L*C1}}$$ Equation 5

The impedance of the loop is preferably 0 ohms over the frequency range of interest, which, in an exemplary operating environment, can be, without limitation between about 30 MHz to about 37.5 MHz. To achieve the desired impedance over the desired frequency range, two or more loops can be stagger tuned as exemplarily shown in FIG. 21.

The resonant frequencies for the loops are based on the bandwidth of interest. If there are two loops, then the loops can be spaced geometrically. In one exemplary non-limiting aspect, the resonant frequency of the first loop is can be about 31 MHz and the resonant frequency of the second loop can be about 36.3 MHz, which corresponds to the pole locations of a second order Butterworth bandpass filter having about −3 dB points at about 30 MHz and about 37.5 MHz. Although FIG. 21 illustrates two loops, it is contemplated that other embodiments can use a different number of loops, which provides coverage for a much wider frequency range. In one aspect, the loops can be spaced logarithmically if there are more than two loops.

FIG. 22 illustrates the assembly of two stagger-tuned loops 1002, 1004 for transmitting the energizing signal to the passive electrical resonant circuit of the assembly and one un-tuned loop 1006 for receiving the output signal. In this aspect, the loops are parallel to one another with the un-tuned loop inside the stagger-tuned loops. Placing the loop used to receive the output signal inside of the loops used to transmit the energizing signal helps to shield the output signal from environmental interferences. In one embodiment, the loops can be positioned within a housing.

One will appreciate that the signal from an implanted passive assembly is relatively weak and is attenuated by the surrounding tissue and the distance between the assembly and the coupling loop. Optimizing the position and angle of the coupling loop relative to the assembly can help maximize the coupling between the assembly and the coupling loop. In one aspect, the coupling loop can be positioned so that a plane defined by the assembly coupling loop is approximately parallel to the inductor within the passive electrical resonant circuit of the assembly and the assembly is approximately centered within the sensor coupling loop. If the coupling loop is not positioned in this manner relative to the inductor, then the strength of the output signal is reduced by the cosine of the angle between the sensor coupling loop and the inductor of the resonant circuit.

In yet another aspect, orientation features can be provided for positioning the coupling loop relative to at least the first assembly to maximize the coupling between the first assembly and the coupling loop. In one aspect, the orientation features can facilitate the placement of the respective assemblies during implantation and the placement of the coupling loop during follow-up examinations. In one aspect, the respective assemblies and the coupling loop can include orientation features that are visible using conventional medical imaging technology. In exemplary aspects, the orientation features on the assemblies can include radiopaque markings and the orientation features on the coupling loop can include a pattern in the ribbing of the housing for the loop.

In one exemplary aspect, to facilitate the proper coupling of the system, the assembly, the assembly housing, and/or the implant can include orientation features, which are visible using a medical imaging technology, such as fluoroscopy, to facilitate the placement of the assemblies during implantation and the coupling loop during follow-up examinations. To position the coupling loop relative to the assembly, the coupling loop is moved or adjusted until a predetermined pattern appears. In one aspect, the orientation features on the coupling loop can be implemented as a pattern in the ribbing of the housing for the loop, which aids in positioning the coupling loop relative to the assembly of the implant. In one aspect, the housing includes an essentially circular section that can be smaller than the diameter of section. When assembled, the sensor coupling and energizing loops are positioned within the ring-shaped section. The orientation features are located in the circular section.

To receive a output signal from the assembly, the physician positions the coupling loop so that the assembly having the passive electrical resonant circuit is positioned approximately at the center of the coupling loop and the angle of the coupling loop is adjusted until the desired orientation of the passive electrical resonant circuit of the assembly and the coupling loop is achieved, which places the inductor coil within the passive electrical resonant circuit essentially parallel to the coupling loop. The orientation feature on the housing can aid in positioning the coupling loop so that the sensor is at approximately the center of the loop.

In one aspect, isolation of the energizing signal and the output signal provided by the base unit and the coupling loop can be maintained in the cable that connects the base unit to the coupling loop. In one aspect, a cable can connect the base unit to the coupling loop and isolate the energizing signal from the output signal. In one aspect, the distal end of the cable that connects to the base unit can comprise a multi-pin connector (e.g., AL06F15-ACS provided by Amphenol) and a right angle housing. The proximal end of the cable that connects to the coupling loop can comprise a first connector, which can be a multi-pin connector (e.g., AMP 1-87631-0 provided by Amphenol) that operably connects to the filtering and switching circuitry associated with the loop; a second connector that operably connects to the energizing loop; and a third connector that operably connects to the loop that couples the signal from the sensor. In this exemplary aspect, the right angle housing and the strain relief provide strain relief at the respective ends of the cable. When assembled with the housing, the strain relief can be positioned proximate to the housing. Optionally, other types of strain relief can be implemented, including, without limitation, physical constraints, such as tie wraps, ferrals or epoxy, and/or service loops. In one aspect, the cable can also comprise ferrite beads, which can help reduce ground currents within the cable.

In one aspect, the position of the coaxial cables within the cable is designed to maximize the isolation between the energizing signal and the sensor signal, while minimizing the diameter of the cable. The cable is configured to maximize the isolation between the coax cable that transmits the energizing signal and the inner bundle and the twisted pairs and the coax cable that receives the sensor signal and the inner bundle.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A method for providing an in-vivo assessment of relative movement of an implant in a living being, the method comprising:
    positioning a first assembly comprising a passive electrical resonant circuit within the living being; and
    positioning a second assembly within the living being spaced from the first assembly;
    selectively electromagnetically coupling the first assembly to an ex-vivo source of RF energy; and
    generating an output signal from the first assembly, in response to the electromagnetic coupling, characterized by a frequency that is dependent upon a distance between the first assembly and the second assembly
    wherein the characterized frequency is the resonant frequency of the first assembly dependent on the distance between the first assembly and the second assembly.

2. The method of claim 1, wherein the second assembly comprises a metallic element.

3. The method of claim 1, wherein the second assembly comprises a non-metallic element.

4. The method of claim 3, wherein the non-metallic element exhibits magnetic properties.

5. The method of claim 1, wherein the second assembly comprises a passive electrical circuit.

6. The method of claim 5, wherein the passive electrical circuit of the second assembly comprises a passive electrical resonant circuit.

7. The method of claim 6, wherein the passive electrical resonant circuit of the second assembly is substantially identical to the passive electrical resonant circuit of the first assembly.

8. The method of claim 6, wherein the passive electrical resonant circuit of the second assembly comprises a LC resonant circuit.

9. The method of claim 8, wherein the passive electrical resonant circuit of the first assembly comprises a LC resonant circuit.

10. The method of claim 9, wherein a resonant frequency of the second assembly differs from a resonant frequency of the first assembly.

11. The method of claim 1, wherein the passive electrical resonant circuit of the first assembly comprises a LC resonant circuit.

12. The method of claim 11, wherein the LC resonant circuit of the first assembly comprises a coil inductor operably coupled to a capacitor.

13. The method of claim 12, wherein the inductance of the LC resonant circuit is between about 5 to about 15 micro-Henry.

14. The method of claim 12, wherein the resonant frequency of the LC resonant circuit is between about 25 to about 45 MHz.

15. The method of claim 12, wherein the capacitance of the LC resonant circuit is between about 1 to about 20 pF.

16. The method of claim 12, wherein, at a first distance between the first assembly and the second assembly, the first assembly generates, in response to the electromagnetic coupling, a first output signal having a first frequency, and wherein, at a second distance between the first assembly and the second assembly that differs from the first distance, the first assembly generates an output signal having a second frequency in response to the electromagnetic coupling that differs from the first frequency.

17. The method of claim 16, wherein the coil inductor is a substantially planar spiral inductor.

18. The method of claim 16, wherein the coil inductor has a longitudinal axis and wherein the coil inducted is elongated about the longitudinal axis.

19. The method of claim 16, wherein at least a portion of each winding of the coil inductor is non-planar with respect to the longitudinal axis.

20. The method of claim 1, wherein at least one of the first assembly and the second assembly is coupled to a portion of the implant.

21. The method of claim 20, wherein at least one of the first assembly and the second assembly is coupled to bone tissue proximate the implant.

22. The method of claim 21, wherein both the first assembly and the second assembly are coupled to spaced portions of the implant.

23. The method of claim 1, wherein a portion of the implant forms the second assembly.

24. The method of claim 23, wherein the portion of the implant forming the second assembly is metallic.

25. The method of claim 1, wherein the implant comprises a prosthetic device for preserving motion between adjacent bones.

26. The method of claim 1, wherein the implant comprises an intervertebral cage.

* * * * *